United States Patent [19]
Bryant et al.

[11] Patent Number: 5,750,708
[45] Date of Patent: May 12, 1998

[54] PYRIDINE COMPOUNDS INTERMEDIATES PROCESSES COMPOSITIONS AND METHODS

[75] Inventors: Henry Uhlman Bryant, Indianapolis; Don Richard Finley, Greenwood; Ken Matsumoto, Indianapolis, all of Ind.

[73] Assignee: Eli Lilly and Company, Indianapolis, Ind.

[21] Appl. No.: 838,098

[22] Filed: Apr. 15, 1997

Related U.S. Application Data

[62] Division of Ser. No. 683,326, Jul. 18, 1996, Pat. No. 5,672,609.
[51] Int. Cl.$^6$ .................................................. C07D 213/02
[52] U.S. Cl. ............................................ 546/334; 546/344
[58] Field of Search ..................................... 546/334, 344

[56]     References Cited

U.S. PATENT DOCUMENTS

| | | | |
|---|---|---|---|
| 4,133,814 | 1/1979 | Jones et al. | 260/326 |
| 4,418,068 | 11/1983 | Jones | 424/267 |

OTHER PUBLICATIONS

Chem. Abs. vol. 106, No. (19) Abstract No. 156,236z (May 1987). Villa et al.

Chem. Abs. vol. 112, No. (17) Abstract No. 158,020x (Apr. 1990). Sonnenschein et al.

*Primary Examiner*—Zinna Northington Davis
*Attorney, Agent, or Firm*—Janelle D. Strode; David E. Boone

[57]     ABSTRACT

The present invention is directed to compounds of Formula I:

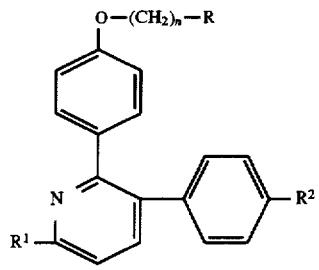

wherein:
  n is 2 or 3;
  R is dimethylamino, diethylamino, 1-piperidinyl, 1-pyrrolidinyl, 4-morpholinyl, or 1-hexamethyleneimino;
  $R^1$ is hydrogen, loweralkyl of $C_1$–$C_4$, phenyl, or mono or di-substituted phenyl wherein each substituent is independently halo, methyl, hydroxy, $C_1$–$C_6$-alkoxy, benzyloxy, $C_1$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, or $C_4$–$C_6$-alkylsulfonyloxy;
  $R^2$ is hydrogen, hydroxy, $C_1$–$C_6$-alkoxy, benzyloxy, $C_1$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, or $C_4$–$C_6$-alkylsulfonyloxy; and the pharmaceutically acceptable acid addition salts, which are for the treatment of post menopausal symptoms such as osteoporosis, cardiovascular conditions such as hyperlipidaemia, and the like.

4 Claims, No Drawings

PYRIDINE COMPOUNDS INTERMEDIATES PROCESSES COMPOSITIONS AND METHODS

This application is a division of application Ser. No. 08/683,326 filed Jul. 18, 1996 now U.S. Pat. No. 5,672,609.

FIELD OF THE INVENTION

This invention relates to the fields of pharmaceutical and organic chemistry and provides novel pyridine compounds which are useful for the treatment of the various medical indications associated with post-menopausal syndrome. The present invention further relates to intermediate compounds and processes useful for preparing the pharmaceutically active compounds of the present invention, and pharmaceutical compositions.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidaemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen.

Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new pyridine compounds, pharmaceutical compositions thereof, and methods of using such compounds for the treatment of post-menopausal syndrome and other estrogen-related pathological conditions.

Smooth aortal muscle cell proliferation plays an important role in diseases such as atherosclerosis and restenosis.

Vascular restenosis after percutaneous transluminal coronary angioplasty (PTCA) has been shown to be a tissue response characterized by an early and late phase.

The early phase occurring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology*, 8: 369–375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal*, 122: 171–187 (July 1991).

In the pathogenesis of restenosis excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use of compounds as smooth aortal muscle cell proliferation inhibitors and, thus inhibitors of restenosis.

BRIEF SUMMARY OF THE INVENTION

The present invention is directed to compounds of Formula I:

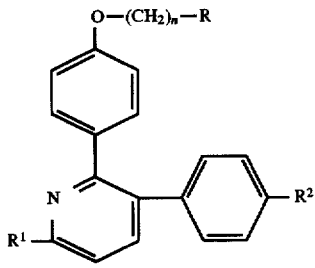

wherein:

n is 2 or 3;

R is dimethylamino, diethylamino, 1-piperidinyl, 1-pyrrolidinyl, 4-morpholinyl, or 1-hexamethyleneimino;

$R^1$ is hydrogen, loweralkyl of $C_1-C_4$, phenyl, or mono or di-substituted phenyl wherein each substituent is independently halo, methyl, hydroxy, $C_1-C_6$-alkoxy, benzyloxy, $C_1-C_6$-alkanoyloxy, benzoyloxy, substituted benzoyloxy bearing 1 to 3 substituents each of which is independently halo, $C_1-C_4$-loweralkyl, or $C_1-C_4$-loweralkoxy, $C_1-C_5$-alkoxycarbonyloxy, or $C_4-C_6$-alkylsulfonyloxy;

$R^2$ is hydrogen, hydroxy, $C_1-C_6$-alkoxy, benzyloxy, $C_1-C_6$-alkanoyloxy, benzoyloxy, substituted benzoyloxy bearing 1 to 3 substituents each of which is independently halo, $C_1-C_4$-loweralkyl, or $C_1-C_4$-loweralkoxy, $C_1-C_5$-alkoxycarbonyloxy, or $C_4-C_6$-alkylsulfonyloxy; and the pharmaceutically acceptable acid addition salts thereof.

These compounds are useful for the treatment of post menopausal symptoms such as osteoporosis, cardiovascular conditions such as hyperlipidaemia, and the like. Accordingly, the present invention is also directed to methods employing and compositions comprising these compounds, for the treatment of post menopausal syndrome. The methods may additionally employ, and the compositions additionally comprise, an estrogen or progestin.

Preferred compounds are those with one or more of the following values, in any combination:

n=2

R=1-pyrrolidinyl

R=1-piperidinyl $R^1$=methyl $R^2$=hydroxy

A particularly preferred compound is 2-[4-[2-(1-pyrrolidinyl) ethoxy]phenyl]-3-(4-hydroxyphenyl)-6-methylpyridine, including pharmaceutically acceptable salts.

Also provided by the present invention is a process for preparing a compound of formula Ia:

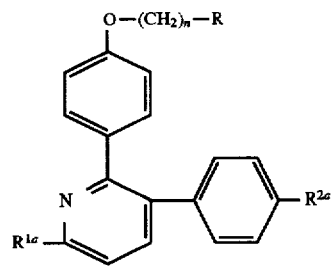

wherein:

n is 2 or 3;

R is dimethylamino, diethylamino, 1-piperidinyl, 1-pyrrolidinyl, 4-morpholinyl, or 1-hexamethyleneimino;

$R^{1a}$ is hydrogen, loweralkyl of $C_1-C_4$, phenyl, or mono- or disubstituted phenyl wherein each substituent is independently halo, methyl, $C_1-C_6$-alkoxy, benzyloxy, $C_1-C_6$-alkanoyloxy, benzoyloxy, substituted benzoyloxy bearing 1 to 3 substituents each of which is independently halo, $C_1-C_4$-loweralkyl, or $C_1-C_4$-loweralkoxy, $C_1-C_5$-alkoxycarbonyloxy, or $C_4-C_6$-alkylsulfonyloxy;

$R^{2a}$ is hydrogen, $C_1-C_6$-alkoxy, benzyloxy, $C_1-C_6$-alkanoyloxy, benzoyloxy, substituted benzoyloxy bearing 1 to 3 substituents each of which is independently halo, $C_1-C_4$-loweralkyl, or $C_1-C_4$-loweralkoxy, $C_1$–$C_5$-alkoxycarbonyloxy, or $C_4$–$C_6$-alkylsulfonyloxy, which comprises reacting a compound of Formula II:

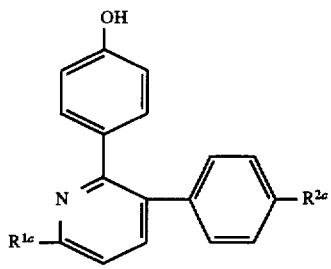

with an alkyl chloride of the formula Cl—$(CH_2)_n$—R, in an inert solvent, in the presence of base, and at a temperature of from 0° to 100° C. The compounds of Formula II are another embodiment of the present invention.

DETAILED DESCRIPTION OF THE INVENTION

The compounds of the present invention are prepared by the following alkylation reaction:

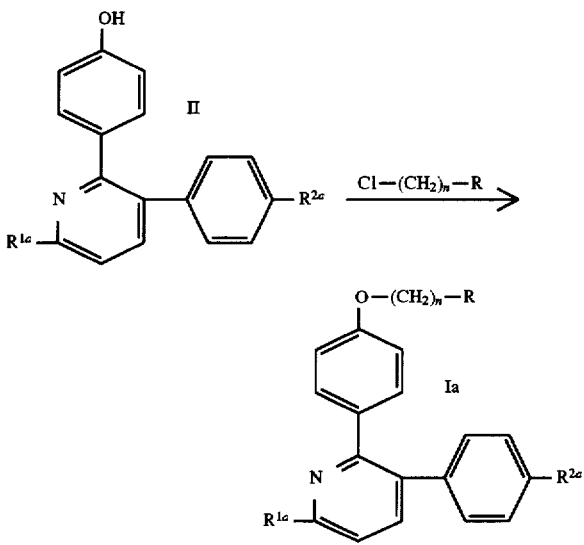

In Formula Ia and II, $R^{1a}$ and $R^{2a}$ have the same meaning as $R^1$ and $R^2$, respectively, except that any hydroxy must be protected; if it is desired to obtain an $R^2$=hydroxy compound, or an $R^1$=hydroxy-substituted phenyl compound, the hydroxy group must first be protected, the alkylation reaction conducted, and the protection later removed.

Hydroxy protection is well known; see, for example, *Protective Groups in Organic Chemistry*, Plenum Press (London and New York, 1973) ; *Protecting Groups in Organic Synthesis*, Wiley (New York, 1981); and *The Peptides*, Vol. I, Schrooder and Lubke, Academic Press (London and New York, 1965). Hydroxyl protection is also discussed in U.S. Pat. No. 4,418,068, which is incorporated herein by reference.

Suitable hydroxy protected groups are $C_1$–$C_6$ alkoxy, benzyloxy, $C_1$–$C_6$-alkanoyloxy, benzoyloxy, substituted benzoyloxy as previously defined, $C_1$–$C_5$-alkoxycarbonyloxy, and $C_4$–$C_6$-alkylsulfonyloxy.

The alkylation reaction is carried out by contacting the reactants, typically in an inert solvent. Suitable such solvents include methyl ethyl ketone, acetone, THF, dimethylformamide, and DMSO. A base is supplied to serve as a hydrogen halide acceptor. The reaction goes forward at temperatures over a wide range but is generally conducted at temperatures from 0° to 100° C. The reaction consumes the reactants and base in equimolar amounts; preferably, the reactants are supplied in equimolar amounts and the base is supplied in an excess amount. Isolation and preparation are carried out in standard procedures.

Deprotection of the hydroxy protecting groups is carried out in known procedures, which are discussed in the references cited above.

The compounds of Formula II are prepared according to the following scheme:

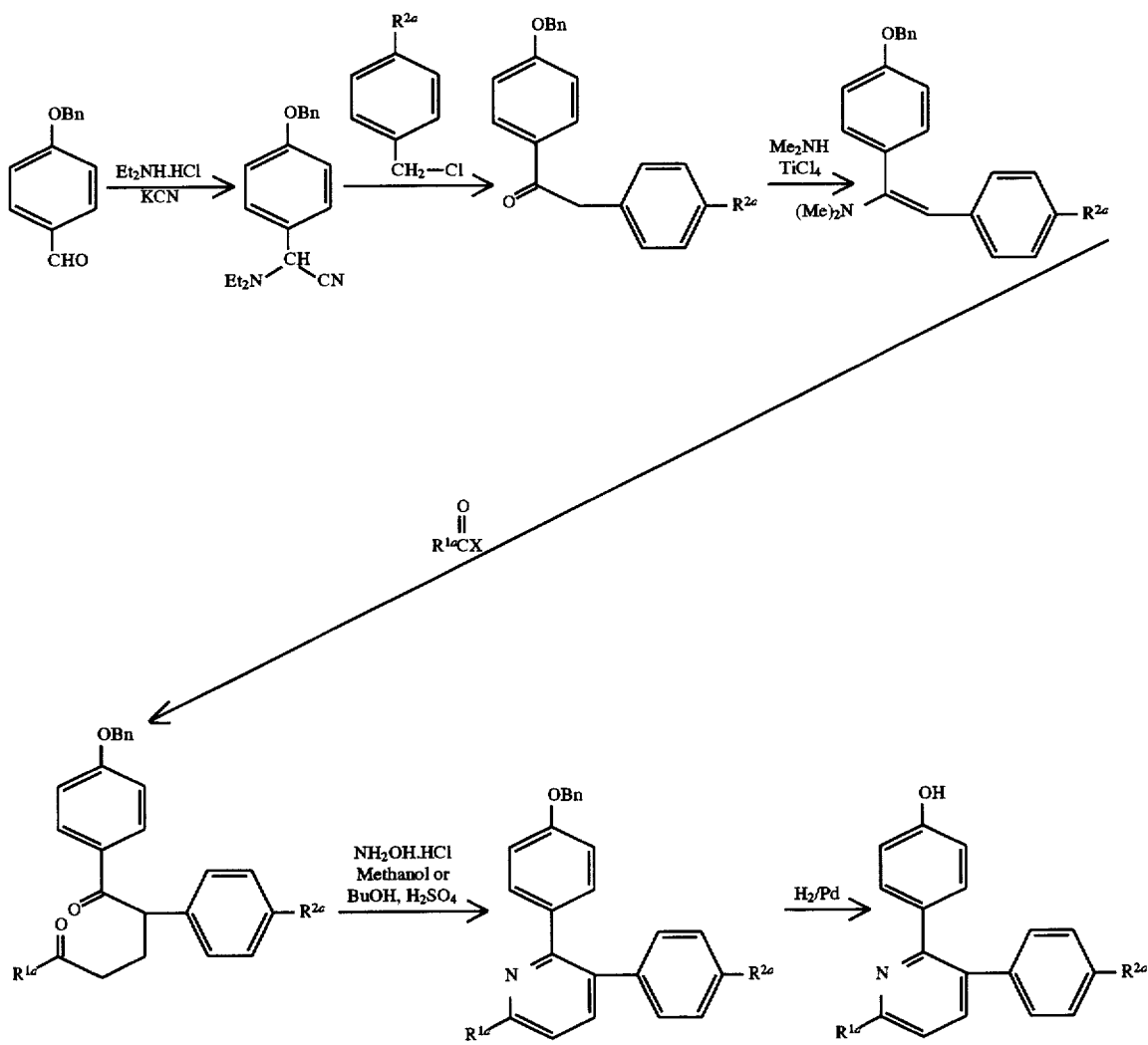

which is illustrated by preparations 1–16. In the formula $$R^{1a}CX,$$

$R^{1a}$ is hydrogen or loweralkyl and X is vinyl, for the preparation of those compounds wherein $R^{1a}$= hydrogen or loweralkyl; or $R^{1a}$ is phenyl or substituted phenyl and X is 2-chloroethyl, for the preparation of those compounds wherein $R^{1a}$=phenyl or substituted phenyl.

Although the free-base form of formula I compounds can be used in the methods of the present invention, it is often preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, napohthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, maionate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with

9 an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

Preparation 1

2-(4-Benzyloxyphenyl)-2-(N,N-diethylamino) acetonitrile

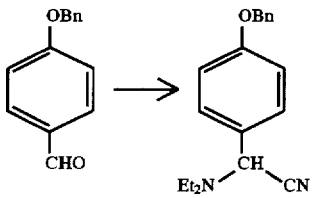

Diethylamine hydrochloride (76.7 g, 70 mmol) was added portion wise at rt to a 200 mL aqueous solution of potassium cyanide (45.5 g, 70 mmol) with stirring and warmed to 60°–65° C. A MeOH/THF (300 ml, 1:1) solution of 4-(benzyloxy)-benzaldehyde (100 g, 47 mmol) (Aldrich) was added in a thin stream to the aqueous solution and stirred for 16 hr at ~62° C. The reaction mixture was allowed to cool and the organics were removed in vacuo. The aqueous portion was diluted with an equal volume of brine and extracted several times with EtOAc. The EtOAc extracts were combined, washed with H$_2$O, dried (Na$_2$SO$_4$), and concentrated to a tacky amber solid. The material was triturated with petroleum ether and filtered to give a yellow solid, which was taken up in warm Et$_2$O, charcoaled, filtered, diluted with petroleum ether, and allowed to crystallize. The crystals were filtered and dried in vacuo to give 81.5 g (59%) of the desired product: mp 75°–76° C.; $^1$H NMR (CDCl$_3$) d 1.06–1.11 (t, 6H, J=7 Hz, CH$_3$), 2.42–2.49 (m, 2H, NCH$_2$), 2.66–2.73 (m, 2H, NCH$_2$), 4.98 (s, 1H, CHCN), 5.09 (s, 2H, OCH$_2$), 6.99–7.01 (d, 2H, J=7 Hz, ArH), 7.35–7.49 (m, 7H,ArH); MS(FD) 294(M$^+$). Anal. Calcd for C$_{19}$H$_{22}$N$_2$O: C, 77.52; H, 7.53; N, 9.51. Found: C, 77.70; H, 7.64; N, 9.45.

10

Preparation 2

4-Methoxybenzylchloride

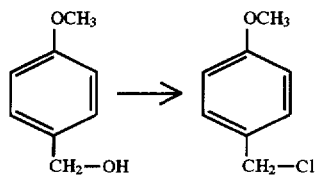

4-Methoxybenzylalcohol (50 g, 0.36 mol) (Aldrich) was added dropwise to 100 mL of conc. HCl and stirred vigorously for 2 h at rt. The reaction mixture was extracted four times with Et$_2$O, the Et$_2$O extracts were combined, washed with brine, dried (Na$_2$SO$_4$), and concentrated. The yellow oil was distilled at 70°–73° C. (0.2 mmHg) to give 52 g (93%) as a colorless oil: $^1$H NMR (CDCl$_3$) d 3.85 (s, 3H, OCH$_3$), 4.62 (s, 2H, CH$_2$Cl), 6.91–6.93 (d, 2H, J=8 Hz, ArH), 7.38–7.40 (d, 2H, J=8 Hz, ArH) ; MS(FD) 156(M+).

Preparation 3

1-(4-Benzyloxyphenyl)-2-(4-methoxyphenyl)ethan-1-one

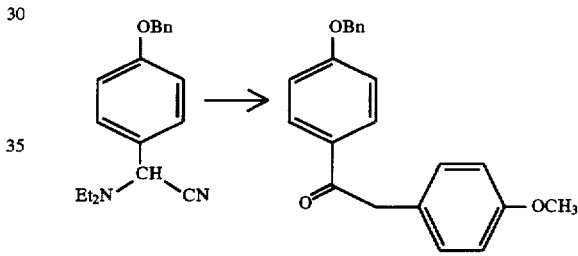

A 60% dispersion of sodium hydride in mineral oil (17 g, 0.42 mol) was washed with hexane and suspended in 200 mL DMF. 2-(4-benzyloxyphenyl) -2-(N,N-diethylamino) acetonitrile (94 g, 0.32 mol) in 350 mL DMF was added dropwise over 1 h at rt to the NaH suspension and stirred an additional 1 h. A 300 mL DMF solution of 4-methoxybenzylchloride (50 g, 0.32 mol) was added dropwise over 45 min to the reaction mixture causing a mild exotherm to 45°. The reaction mixture was stirred for 16 h at rt, cooled in an ice bath, quenched with 100 mL MeOH, and reduced in vacuo to a smaller volume. The brown suspension was cooled in an ice bath and stirred while 2 L of 5N HCl was added at a rate to keep the temperature below 25° C. The suspension was stirred 18 h at rt, then extracted several times with CH$_2$Cl$_2$. The CH$_2$Cl$_2$ extracts were combined, washed with brine, dried (Na$_2$SO$_4$), and concentrated to give an oily brown solid. The product was triturated with Et$_2$O, filtered, and dried in vacuo to give 90 g (85%) of an off-white solid: mp 147°–148° C.; $^1$H NMR (CDCl$_3$) d 3.80 (s, 3H, OCH$_3$), 4.18 (s, 2H, O=CCH$_2$), 5.13 (s, 2H, OCH$_2$Ar), 7.00–7.03 (d, 2H, J=9 Hz, ArH), 7.18–7.21 (d, 2H, J=9 Hz, ArH), 7.41–7.44 (m, 5H, ArH), 7.99–8.02 (d, 2H, J 9 Hz, ArH) ; MS(FD) 332(M$^+$). Anal. Calcd for C$_{22}$H$_{20}$O$_3$: C, 79.49; H, 6.06. Found: C, 79.23); H, 6.08.

Preparation 4

1-(4-Benzyloxyphenyl)-1-((dimethylamino)-2-(4-methoxyphenyl)ethylene

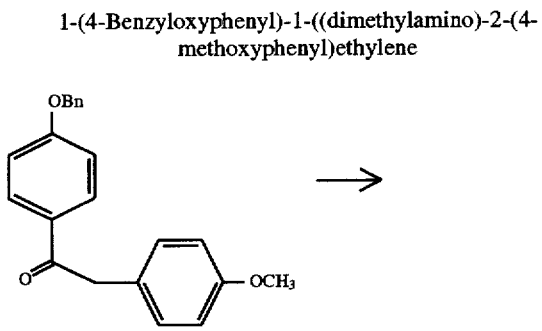

Dimethylamine (55 mL, 0.15 mol) in 100 mL of toluene was added over ten min at 0°–5° C. to a 600 mL toluene suspension of 1-(4-benzyloxyphenyl)-2-(4-methoxyphenyl) ethan-1-one (50 g, 0.15 mol), then stirred 15 min at 0° C. A 50 mL toluene solution of TiCl$_4$ (9.8 mL, 0.09 mol) was added dropwise over 1 h to the reaction mixture, keeping the temperature below 5° C. The brown suspension was stirred 16 h at rt then filtered through Hyflo Super Cel to give a yellow filtrate. Two Et$_2$O washes of the filter bed were combined with the filtrate and the solution was concentrated to a thick amber oil. The oil was triturated with Et$_2$O/pet. ether and filtered to give 41 g (77%) of yellow solid: mp 60° C.; $^1$H NMR (CDCl$_3$) d 2.64 (s, 6H, NMe$_2$), 3.71 (s, 3H, OCH$_3$), 5.07 (s, 2H, OCH$_2$), 5.42 (s, 1H, =CH), 6.57–6.60 (d, 2H, J=9 Hz, ArH), 6.67–6.70 (d, 2H, J=9 Hz, ArH), 6.86–6.89 (d, 2H, J=9 Hz, ArH), 6.90–6.93 (d, 2H, J=9 Hz, ArH), 7.18–7.21 (d, 2H, J=9 Hz, ArH), 7.40–7.45 (m, 5H, ArH); MS(FD) 360[M+1]$^+$. Anal. Calcd for C$_{24}$H$_{25}$NO$_2$: C, 80.19; H, 7.01; N, 3.90. Found: C, 80.41; H, 7.12; N, 4.09.

Preparation 5

1-(4-Benzyloxyphenyl)-2-(4-methoxyphenyl) hexan-1,5-dione

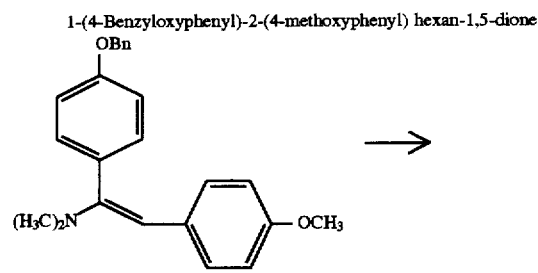

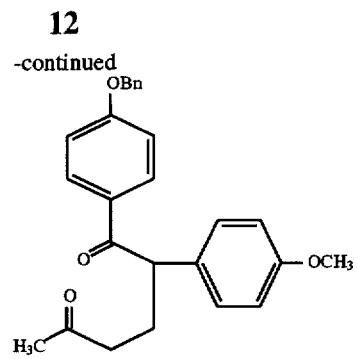

Methyl vinyl ketone (25 mL, 31 mmol) (Aldrich) was added to a 250 mL MeCN solution of 1-(4-benzyloxyphenyl)-1-dimethylamino-2-(4-methoxyphenyl) ethylene (28 g, 80 mmol) and refluxed 24 h. The reaction mixture was allowed to cool and concentrated to a gummy solid, which was then stirred for 16 h in 200 mL of 4N HCl. The aqueous mixture was extracted several times with EtOAc. The EtOAc extracts were combined, washed with brine, and concentrated to a solid. Recrystallisation from EtOAc/hexane gave 27.3 g (87%) of the desired product: mp 93°–94° C.; $^1$H NMR (CDCl$_3$) d 2.08–2.41 (comp, 7H, O=CCH$_3$, CH$_2$CH$_2$), 3.75 (s, 3H, OCH$_3$), 4.54–4.57 (t, 1H, J=4, Hz, CH), 5.08 (s, 2H, OCH$_2$Ar), 6.80–6.83 (d, 2H, J=9 Hz, ArH), 6.91–6.94 (d, 2H, J=9 Hz, ArH), 7.16–7.19 (d, 2H, J=9 Hz, ArH), 7.34–7.39 (m, 5H, ArH), 7.92–7.95 (d, 2H, J=9 Hz, ArH); MS(FD) 402(M$^+$). Anal. Calcd for C$_{26}$H$_{26}$O$_4$: C, 77.79; H, 6.61. Found: C, 77.59; H, 6.51.

Preparation 6

1-(4-Benzyloxyphenyl)-2-(4-methoxyphenyl)-5-phenylpentan-1,5-dione

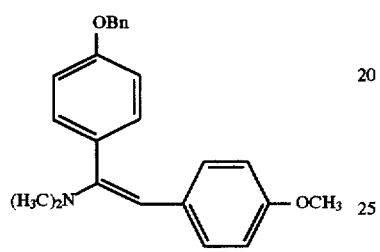

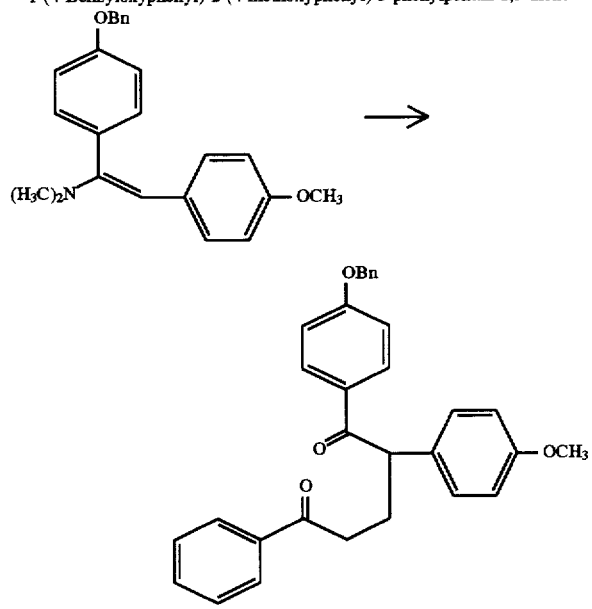

1-(4-Benzyloxyphenyl)-1-dimethylamino-2-(4-methoxyphenyl)ethylene (5.03 g, 14 mmol) and 3-chloroporopiophenone (2.47 g, 15 mmol) (Aldrich) were refluxed in 60 mL MeCN for 18 h, then worked up and purified to give 5.18 g (79%) of product: mp 76°–78° C.; $^1$H NMR (CDCl$_3$) d 2.22–3.00 (comp, 4H, CH$_2$CH$_2$), 3.75 (s, 3H, OCH$_3$), 4.64–4.69 (t, 1H, J=7 Hz, CH), 5.08 (s, 2H, OCH$_2$Ar), 6.80–6.83 (d, 2H, J=9 Hz, ArH), 6.92–6.94 (d, 2H, J=9 Hz, ArH), 7.20–7.54 (comp, 10H, ArH), 7.89–7.98 (m, 4H, ArH) ; MS(FD) 464(M⁺). Anal. Calcd for $C_{31}H_{28}O_4$: C, 80.15; H, 6.07. Found: C, 80.38; H, 6.15.

Preparation 7

1-(4-Benzyloxyphenyl)-2-(4-methoxyphenyl)-5-(4-fluorophenyl)pentan-1,5-dione

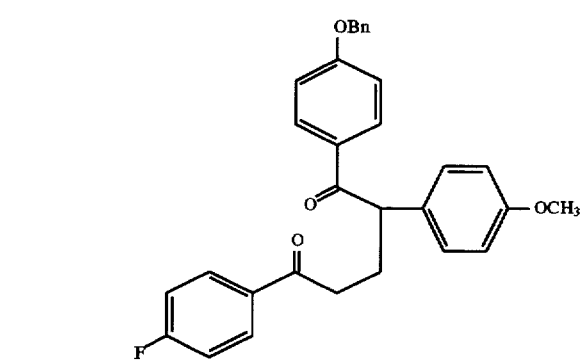

The 1-(4-benzyloxyphenyl)-1-dimethylamino-2-(4-methoxyphenyl)ethylene (5.4 g, 15 mmol) and 3-chloro-4'-fluoropropiophenone (3.1 g, 17 mmol) (Aldrich) were refluxed in 60 mL MeCN for 20 h and then the reaction mixture worked up and purified to give 4.2 g (66%) of white solid: mp 90°–93° C.; ¹NMR (CDCl3) d 2.21–2.98 (comp, 4H, CH₂CH₂), 3.76 (s, 3H, OCH₃), 4.63–4.68 (t, 1H, J=7 Hz, CH), 5.09 (s, 2H, OCH₂Ar), 6.81–6.84 (d, 2H, J=9 Hz, ArH), 6.92–6.95 (d, 2H, J=9 Hz, ArH), 7.08–7.40 (comp, 9H, ArH), 7.92–7.98 (m, 4H, ArH); FD(MS) 482(M⁺). Anal. Calcd for $C_{31}H_{27}O_4F$: C, 77.16; H, 5.64. Found: C, 77.22; H, 5.72.

Preparation 8

1-(4-Benzyloxyphenyl)-2,5-bis(4-methoxyphenyl)pentan-1,5-dione

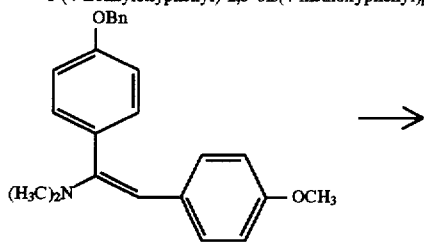

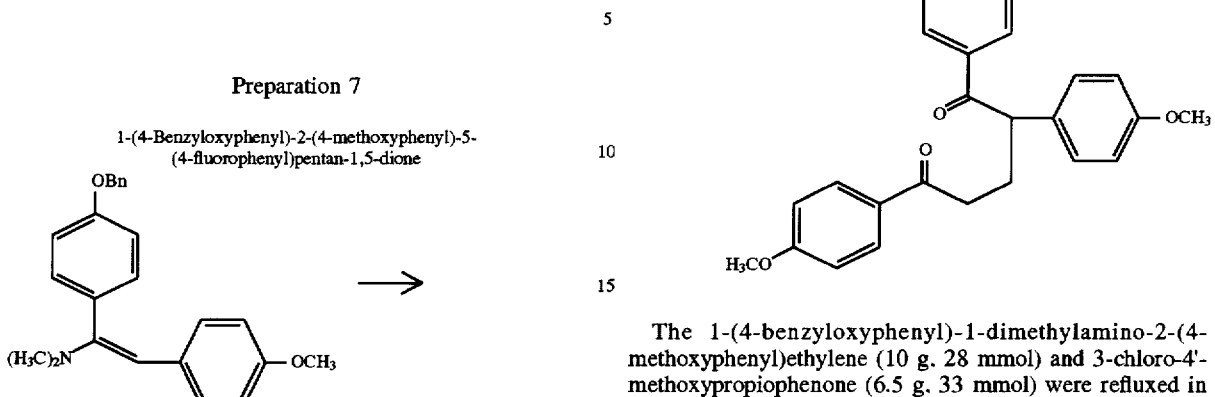

The 1-(4-benzyloxyphenyl)-1-dimethylamino-2-(4-methoxyphenyl)ethylene (10 g, 28 mmol) and 3-chloro-4'-methoxypropiophenone (6.5 g, 33 mmol) were refluxed in 150 mL MeCN for 24 h, then the reaction mixture was worked up and purified to give 10 g (72%) of product: mp 132°–134° C.; ¹H NMR (CDCl₃) d 2.20–2.98 (comp, 4H, CH₂CH₂), 3.75 (s, 3H, OCH₃), 4.64–4.69 (t, 1H, J=7 Hz, CH), 5.08 (s, 2H, OCH₂Ar), 6.81–6.94 (m, 6H, ArH), 7.17–7.42 (m, 7H, ArH), 7.87–8.00 (m, 4H, ArH); MS(FD) 495[M+1]⁺. Anal. Calcd for $C_{32}H_{30}O_5$: C, 77.71; H, 6.11. Found: C, 77.80; H, 6.05.

Preparation 9

2-(4-Benzyloxyphenyl)-3-(4-methoxyphenyl)-6-methylpyridine

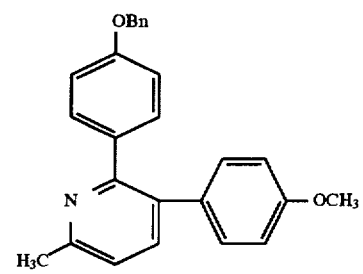

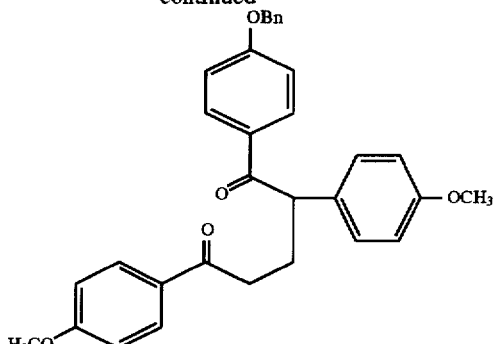

1-(4-Benzyloxylphenyl)-2-(4-methoxyphenyl)hexan-1,5-dione (10 g, 0.025 mol) was dissolved in 300 mL MeOH, hydroxylamine hydrochloride (2.16 g, 0.031 mol) was added, and the reaction mixture was refluxed for 18 h. The reaction mixture was allowed to cool, most of the MeOH removed in vacuo, and then was diluted with 250 mL water. The aqueous mixture was extracted several times with EtOAc, the EtOAc extracts were combined, washed with brine, dried (Na₂SO₄), and concentrated. The residue was purified by prep. chromatography (EtOAc/hexane gradient) and recrystallised from EtOAc/hexane to give 4.4 g (47%) of product: mp 135°–136° C.; ¹H NMR (CDCl₃) d 2.74 (s, 3H, Pyr-CH₃), 3.92 (s, 3H, OCH₃), 5.16 (s, 2H, OCH₂Ar), 6.91–6.98 (m, 4H, ArH), 7.18–7.25 (m, 3H, ArH), 7.37–7.52

(m, 7H, ArH), 7.66–7.68 (d, 1H, J=8 Hz, ArH); MS(FD) 381(M⁺). Anal. Calcd for $C_{26}H_{23}N_2$: C, 81.86; H, 6.08; N, 3.67. Found: C, 82.10, H, 6.21; N, 3.71.

Preparation 10

2-(4-Benzyloxyphenyl)-3-(4-methoxyphenyl)-6-phenylpyridine

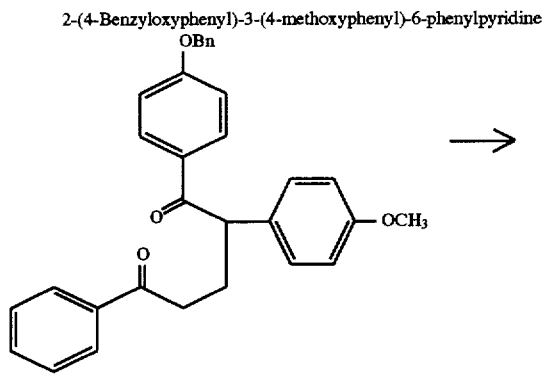

The 1-(benzyloxyphenyl)-2-(4-methoxyphenyl)-5-phenylpentan-1,5-dione (1.0 g, 2.2 mmol) and hydroxylamine hydrochloride (0.3 g, 4.3 mmol) were refluxed in 30 mL of MeOH for 48 h, worked up, purified, and recrystallised from Et₂O/pet. ether to give 0.32 g (34% yield) of white solid: mp 130°–132° C.; ¹H NMR (CDCl₃) d 3.82 (s, 3H, OCH₃), 5.06 (s, 2H, OCH₂Ar), 6.84–6.90 (m, 4H, ArH), 7.15–7.18 (d, 2H, J=9, ArH), 7.38–7.49 (comp, 10H, ArH), 7.73 (s, 2H, ArH), 3.12–8.15 (d, 2H, J=9, ArH); MS(FD) 443(M⁺). Anal. Calcd for $C_{31}H_{25}NO_2$: C, 83.94; H, 5.68; N, 3.16. Found: C, 84.14; H, 5.90; N, 2.94.

Preparation 11

2-(4-Benzyloxyphenyl)-3-(4-methoxyphenyl)-6-(4-fluorophenyl)pyridine

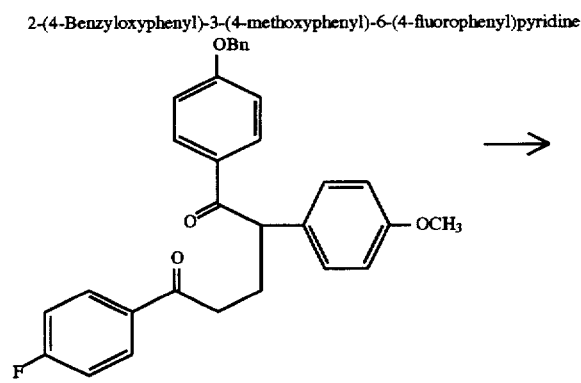

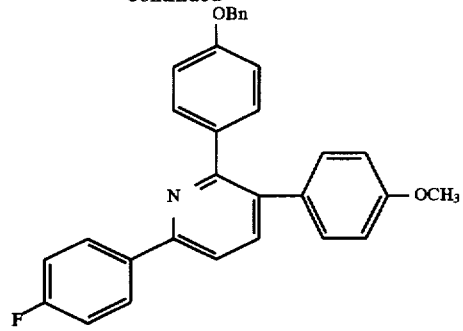

The 1-(4-benzyloxyphenyl)-2-(4-methoxyphenyl)-5-(4-fluorophenyl)pentan-1,5-dione (1.0 g, 2.4 mmol) and hydroxylamine hydrochloride (0.2 g, 2.9 mmol) were refluxed in 30 mL of MeOH for 48 h, worked up, and purified to give 0.45 g (40 % yield) of product: mp 114°–115° C.; ¹H NMR (CDCl₃) d 3.82 (s, 3H, OCH₃), 5.06 (s, 2H, OCH₂Ar), 6.83–6.89 (m, 4H, ArH), 7.13–7.19 (m, 4H, ArH), 7.34–7.44 (m, 7H, ArH), 7.65–7.74 (dd, 2H, J=8, ArH), 8.10–8.14 (m, 2H, ArH); MS(FD) 461(M⁺). Anal. Calcd for $C_{31}H_{24}NO_2F$: C, 80.67; H, 5.24; N,3.03. Found: C, 80.87; H, 5.30; N, 3.09.

Preparation 12

2-(4-Benzyloxyphenyl)-3,6-bis(4-methoxyphenyl)pyridine

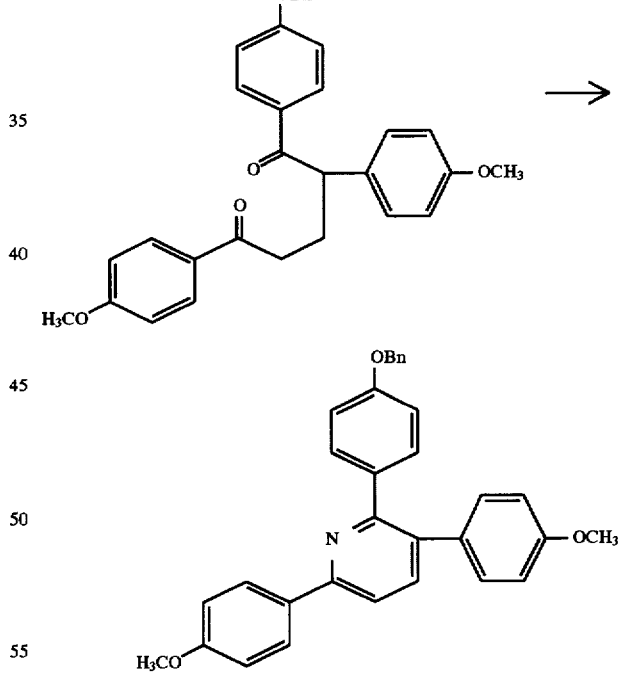

The 1-(4-benzyloxyphenyl)-2,5-bis(4-methoxyphenyl)pentan-1,5-dione (9 g, 18 mmol), hydroxylamine hydrochloride (1.8 g, 26 mmol), and 0.8 mL concd H₂SO₄ were stirred in 250 mL of 1-butanol at 95°–100° C. for 18 h. The reaction mixture was neutralized with solid NaHCO₃, worked up, purified, and recrystallised (EtOAC/hexane) to give 3.2 g (37% yield) of white solid: mp 99°–102° C.; ¹H NMR (CDCl₃) d 3.82 (s, 3H, OCH₃), 3.87 (s, 3H, OCH3), 5.06 (s, 2H, OCH₂Ar), 6.83–6.89 (m, 4H, ArH), 6.99–7.02 (d, 2H, J=9, ArH), 7.14–7.17 (d, 2H, J=9, ArH), 7.32–7.45 (m, 7H, ArH), 7.64–7.71 (m, 2H, ArH), 8.08–8.11 (d, 2H, J=9, ArH); MS(FD) 473(M⁺). Anal. Calcd for C₃₂H₂₇NO₃: C, 81.16; H, 5.75; N, 2.96. Found: C, 81.10; H, 5.92; N, 2.98.

Preparation 13

2-(4-Hydroxyphenyl)-3-(4-methoxyphenyl)-6-methylpyridine

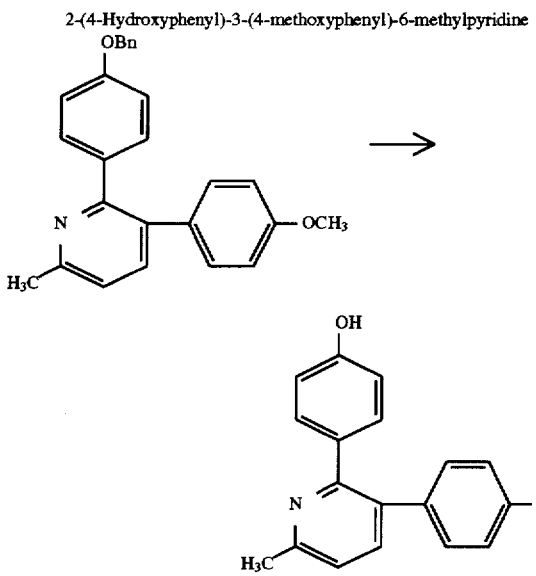

The 2-(4-benzyloxyphenyl)-3-(4-methoxyphenyl)-6-methylpyridine (14 g, 0.37 mmol) and ammonium formate (3.5 g, 55 mmol) were stirred in 1 L of EtOH, then 5% Pd/C (5.8 g, 3 mmol Pd) was added and the reaction mixture warmed to 50°–55° C. The reaction mixture was stirred at 55° C. for 1 h at which time the TLC (MeOH/CHCl₃, 1:9) indicated the starting material was consumed. After cooling, the reaction mixture was filtered, concentrated, and the residue triturated with Et₂O to give 9.6 g (90% yield) of white solid: MP 190 OC; ¹H NMR (CDCl₃) d 2.66 (s, 3H, Pyr-CH₃), 3.82 (s, 3H, OCH₃), 6.53–6.56 (d, 2H, J=8 Hz, ArH), 6.80–6.83 (Id, 21H, J=8 Hz, ArH), 7.06–7.18 (m, 6H, ArH, ArOH), 7.59–7.62 (d, 1H, J=8 Hz, ArH); MS(FD) 291(M⁺). Anal. Calcd for C₁₉H₁₇NO₂: C, 78.33; H, 5.88; N, 4.81. Found: C, 78.11; H, 5.93; N, 4.72.

Preparation 14

2-(4-Hydroxyphenyl)-3-(4-methoxyphenyl)-6-phenylpyridine

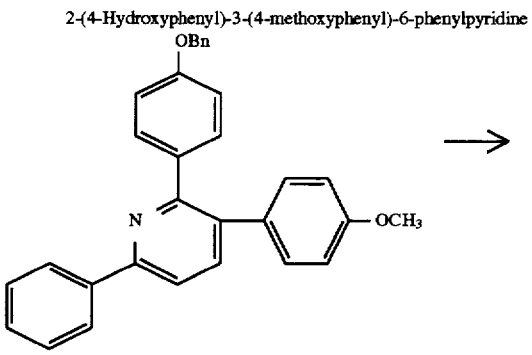

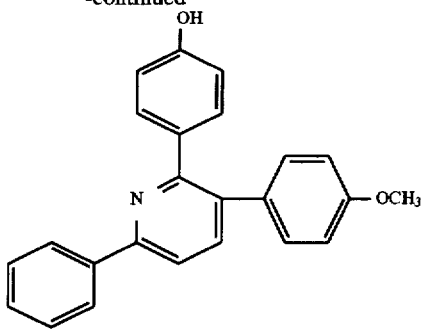

The 2-(4-benzyloxyphenyl)-3-(4-methoxyphenyl)-6-phenylpyridine (3.5 g, 7.9 mmol) and ammonium formate (2.5 g, 40 mmol) were stirred in 150 mL of EtOH, then 5% Pd/C (1.4 g, 0.6 mmol Pd) was added and the reaction mixture was stirred at 60° C. for 1 h. The TLC (MeOH/CHCl₃, 1:9) indicated a small amount of the starting material remained, so more ammonium formate (0.3 g, 5 mmol) was added and reaction mixture stirred at 60° C. for 0.5 h, which consumed the remaining starting material. After cooling, the reaction mixture was filtered and the filter pad washed with 50 mL of EtOH, then 50 mL of EtOAc. The filtrates were combined and concentrated, then redissolved in 150 mL of EtOAc, washed with brine, dried (Na₂SO₄), concentrated, and the residue triturated with Et₂O/pet. ether to give 2.5 g (90% yield) of white solid: mp 200°–202° C.; ¹H NMR (CDCl₃) d 3.85 (s, 3H, OCH₃), 5.07 (s, 1H, ArOH), 6.71–6.90 (m, 4H, ArH), 7.17–7.20 (d, 2H, J=8 Hz, ArH), 7.38–7.54 (m, 5H, ArH), 7.75 (s, 2H, ArH), 8.13–8.16 (d, 2H, J=9 Hz, ArH) ; MS(FD) 354(M⁺). Anal. Calcd for C₂₄H₁₉NO₂: C, 81.56; H, 5.42; N, 3.96. Found: C, 81.50; H, 5.61; N, 3.99.

Preparation 15

2-(4-Hydroxyphenyl)-3-(4-methoxyphenyl)-6-(4-fluorophenyl)pyridine

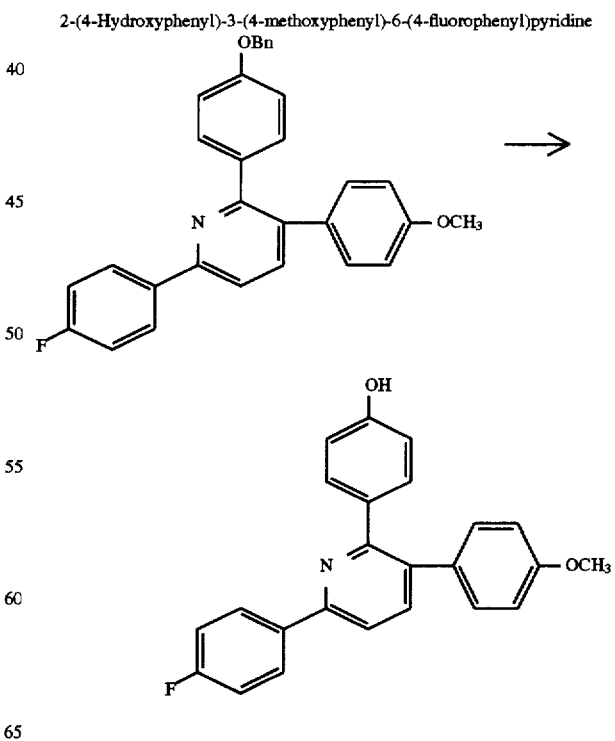

The 2-(4-benzyloxyphenyl)-3-(4-methoxyphenyl)-6-(4-fluorophenyl)pyridine (1.2 g, 2.6 mmol) was dissolved in 50 mL of THF/EtOH (1:1), 5% Pd/C (0.3 g, 0.14 mmol Pd) added, and the reaction mixture hydrogenated at 40 psi for 4 h at rt. The reaction mixture was filtered and concentrated to give 0.86 g (90% yield) of white foam: mp 143°–145° C.; $^1$H NMR (CDCl$_3$) d 3.83 (s, 3H, OCH$_3$), 4.78 (s, 1H, ArOH), 6.72–6.75 (d, 2H, J=8 Hz, ArH), 6.84–6.87 (d, 2H, J=8 Hz, ArH), 7.14–7.27 (m, 4H, ArH), 7.37–7.40 (d, 2H, J=8 Hz, ArH), 7.69–7.73 (m, 2H, ArH), 8.10–8.15 (m, 2H, ArH); MS(FD) 371(M$^+$). Anal. Calcd for C$_{24}$H$_{18}$NO$_2$F: C, 77.61; H, 4.89; N, 3.77. Found: C, 77.88; H, 5.12; N, 3.51.

Preparation 16

2-(4-Hydroxyphenyl)-3,6-bis(4-methoxyphenyl)pyridine

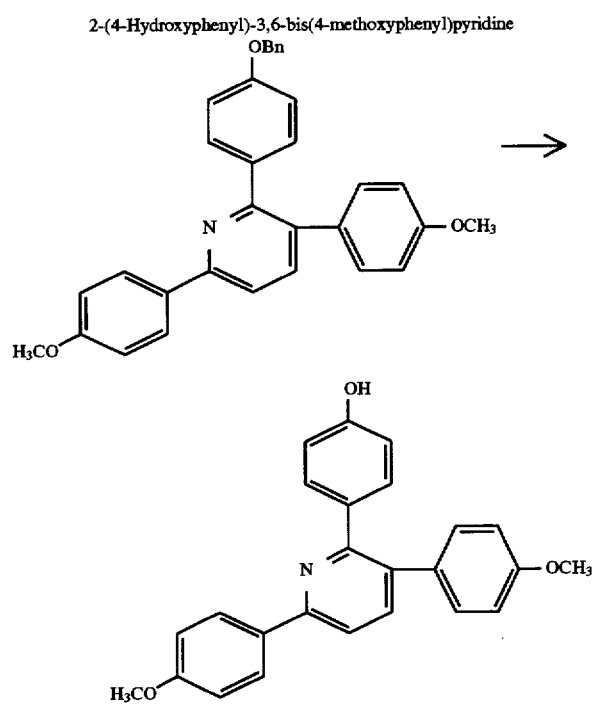

The 2-(4-benzyloxyphenyl)-3,6-bis(4-methoxyphenyl) pyridine (3.0 g, 6.3 mmol), ammonium formate (2.0 g, 31 mmol), and 5% Pd/C (1.0 g, 0.5 mmol Pd) were combined in 150 mL of EtOH, and the reaction mixture was stirred at 50°–55° C. and followed by TLC (EtOAc/Tol, 1:9). After 1 h, more ammonium formate (0.5 g, 8 mmol) was added and reaction mixture stirred at 50° C. for 30 min and no starting material remained. After cooling, the reaction mixture was filtered, concentrated, and the residue triturated with Et$_2$O/ pet. ether. The white ppt was filtered and dried in vacuo to give 2.35g (97% yield) of product: mp 204°–205° C.; $^1$H NMR (CDCl$_3$) d 3.83 (s, 3H, OCH$_3$), 3.88 (s, 3H, OCH$_3$), 4.85 (s, 1H, ArOH), 6.71–6.74 (d, 2H, J=9 Hz, ArH), 6.83–6.86 (d, 2H, J=9 Hz, ArH), 7.00–7.03 (d, 2H, J=9 Hz, ArH), 7.14–7.17 (d, 2H, J=9 Hz, ArH), 7.37–7.40 (d, 2H, J=9 Hz, ArH), 7.68–7.70 (m, 2H, ArH), 8.08–8.11 (d, 2H, J=9 Hz, ArH); MS(FD) 383($^+$). Anal. Calcd for C$_{25}$H$_{21}$NO$_3$: C, 78.31; H, 5.52; N, 3.65. Found: C, 78.07; H, 5.79; N, 3.95.

EXAMPLE 1

2-[4-[2-(1-N,N-Dimethylamino)ethoxy]phenyl]-3-(4-methoxyphenyl)-6-methylpyridine

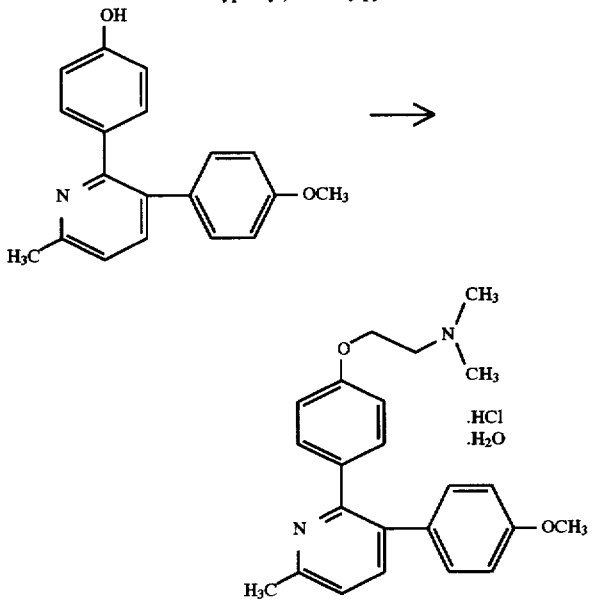

The 2-(4-hydroxyphenyl)-3-(4-methoxyphenyl)-6-methylpyridine (3, 5g, 12 mmol), 2-dimethylaminoethylchloride hydrochloride (1.73 g, 12 mmol), and powdered K$_2$CO$_3$ (8.3 g, 60 mmol) were stirred in 250 mL methyl ethyl ketone and refluxed 20 h. The reaction mixture was worked up and purified by prep. chromatography (EtOH/CH$_2$Cl$_2$ gradient) to give 3.7 g (85% yield) as a clear gum. A portion of the gum (1.6 g, 4.4 mmol) was dissolved in 50 mL MeOH, 30 mL HCl/MeOH was added at 0° C., stirred 10 min, worked up and triturated with Et$_2$O, then filtered and dried in vacuo to give 1.48 g (84 % conversion of free base to salt) as the HCl salt monohydrate: mp 135°–140° C.; $^1$H NMR (CDCl$_3$) d 1.60–1.90 (bs, 2H, H$_2$O), 2.92–2.93 (bs, 6H, NCH$_3$), 3.13 (s, 3H, pyr-CH$_3$), 3.47–3.49 (m, 2H, CH$_2$N), 3.82 (s, 3H, ArOCH$_3$), 4.50–4.53 (m, 2H, OCH$_2$), 6.85–6.90 (m, 4H, ArH), 7.00–7.04 (m, 2H, ArH), 7.41–7.44 (m, 2H, ArH), 7.54–7.56 (d, 1H, J=8 Hz, ArH), 8.12–8.14 (d, 1H, J=8 Hz, ArH); MS(FAB) 363 (M$^+$). Anal. Calcd for C$_{23}$H$_{26}$N$_2$O$_2$.HCl.H$_2$O: C, 66.26; H, 7.01; N, 6.72. Found: C, 66.54; H, 6.72; N, 6.79.

EXAMPLE 2

2-[4-[2-(1-Pyrrolidinyl)ethoxy]phenyl]-3-(4-methoxyphenyl)-6-methylpyridine

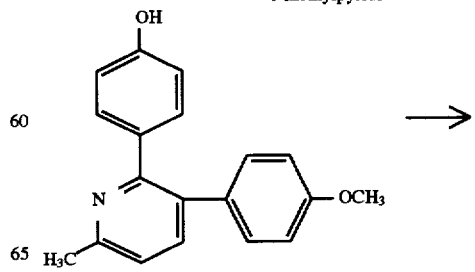

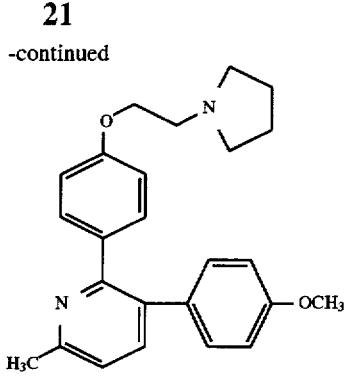

The 2-(4-hydroxyphenyl)-3-(4-methoxyphenyl)-6-methylpyridine (4 g, 14 mmol), N-(2-chloroethyl) pyrrolidine hydrochloride (2.3 g, 14 mmol), and powdered $K_2CO_3$ (9.5 g, 68 mmol) were stirred in 250 mL methyl ethyl ketone and refluxed 18 h. The reaction mixture was worked up and purified by prep. chromatography (EtOH/$CH_2Cl_2$ gradient), triturated with $Et_2O$, filtered, and dried in vacuo to give 3.7 g (71% yield) of white product: mp 63°–64° C.; $^1$H NMR (CDCl$_3$) d 1.79–1.83 (comp, 4H, pyrrolidine), 2.60–2.64 (comp, 7H, Pyr-CH$_3$ and pyrrolidine), 2.86–2.90 (t, 2H, J=6 Hz, NCH$_2$), 3.81 (s, 3H, ArOCH$_3$), 4.07–4.11 (t, 2H, J=6 Hz, OCH$_2$), 6.78–6.82 (m, 4H, ArH), 7.06–7.30 (comp, 5H, ArH), 7.55–7.58 (d, 1H, J=8 Hz, ArH); MS(FD) 388(M$^+$). Anal. Calcd for $C_{25}H_{28}N_2O_2$: C, 77.23; H, 72.6; N, 7.21. Found: C, 77.12; H, 7.48; N, 7.00.

EXAMPLE 3

2-{4-[2-(4-Morpholinyl)ethoxy]phenyl}-3-(4-methoxyphenyl)-6-methylpyridine

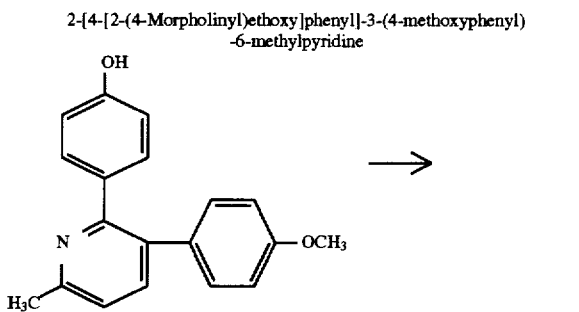

The 2-(4-hydroxyphenyl)-3-(4-methoxyphenyl)-6-methylpyridine (3.0 g, 10 mmol), N-(2-chloroethyl) morpholine hydrochloride (1.9 g, 10 mmol), and powdered $K_2CO_3$ (7.1 g, 51 mmol) were stirred in 200 mL methyl ethyl ketone and refluxed 20 h. The reaction mixture was worked up and purified by prep. chromatography (EtOH/$CH_2Cl_2$ gradient), triturated with $Et_2O$/pet. ether, filtered, and dried in vacuo to give 3.4 g (82% yield) of white solid: mp 66°–67° C.; $^1$H NMR (CDCl$_3$) d 2.55–2.58 (m 4H, morpholine), 2.62 (s, 3H, pyr-CH$_3$), 2.76–2.80 (t, 2H, J=6 Hz, NCH$_2$), 3.72–3.75 (m, 4H, morpholine), 3.80 (s, 3H, ArOCH$_3$), 4.06–4.10 (t, 2H, J=6 Hz, OCH$_2$), 6.75–6.81 (m, 4H, ArH), 7.05–7.14 (m, 4H, ArH), 7.26–7.29 (m, 1H, ArH) 7.54–7.56 (d, 1H, J=8 Hz, ArH); MS(FD) 404(M$^+$). Anal. Calcd for $C_{25}H_{28}N_2O_3$: C, 74.23; H, 6.98; N, 6.93. Found: C, 74.50; H, 6.91; N, 7.05.

EXAMPLE 4

2-{4-[2-(1-Pyrrolidinyl)ethoxy]phenyl}-3-(4-methoxyphenyl)-6-phenylpyridine

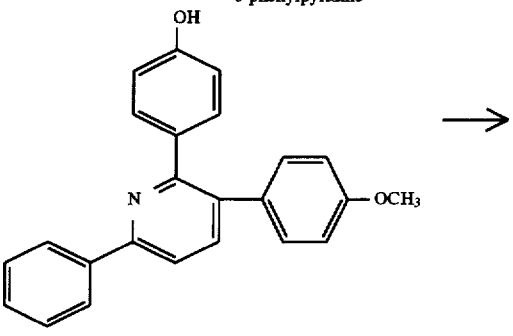

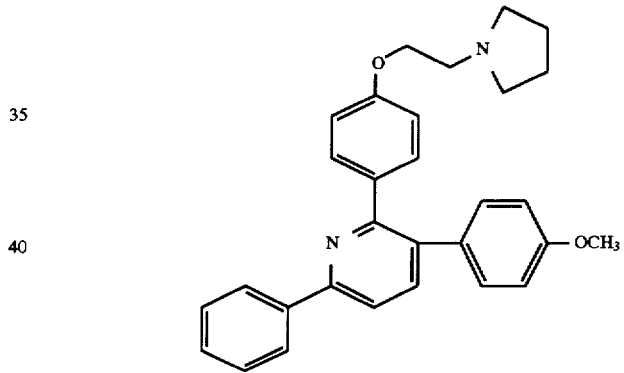

The 2-(4-hydroxyphenyl)-3-(4-methoxyphenyl)-6-phenylpyridine (2.0 g, 5 mmol), N-(2-chloroethyl) pyrrolidine hydrochloride (1.0 g, 5 mmol), and powdered $K_2CO_3$ (4.2 g, 30 mmol) were stirred in 200 mL methyl ethyl ketone and refluxed 20 h. The reaction mixture was worked up and the residue triturated with pet. ether, filtered, and dried in vacuo to give 2.1 g (84% yield) of an off-white solid: mp 100°–103° C.; $^1$H NMR (CDCl$_3$) d 1.81–1.84 (m, 4H, pyrrolidine), 2.61–2.65 (m, 4H, pyrrolidine), 2.88–2.92 (t, 2H, J=6 Hz, NCH$_2$), 3.83 (s, 3H, ArOCH$_3$), 4.10–4.14 (t, 2H, J=6 Hz, OCH$_2$), 6.81–6.87 (m, 4H, ArH), 7.15–7.18 (d, 2H, J=9 Hz, ArH) 7.42–7.50 (m, 5H, ArH), 7.73 (s, 2H, ArH), 8.13–8.16 (d, 2H, J=9 Hz, ArH); MS(FD) 450(M$^+$). Anal. Calcd for $C_{30}H_{30}N_2O_2$: C, 79.97; H, 6.71; N, 6.22. Found: C, 79.86; H, 6.09; N, 6.16.

EXAMPLE 5

2-[4-[2-(1-Pyrrolidinyl)ethoxy]phenyl]-3,6-bis(4-methoxyphenyl)pyridine

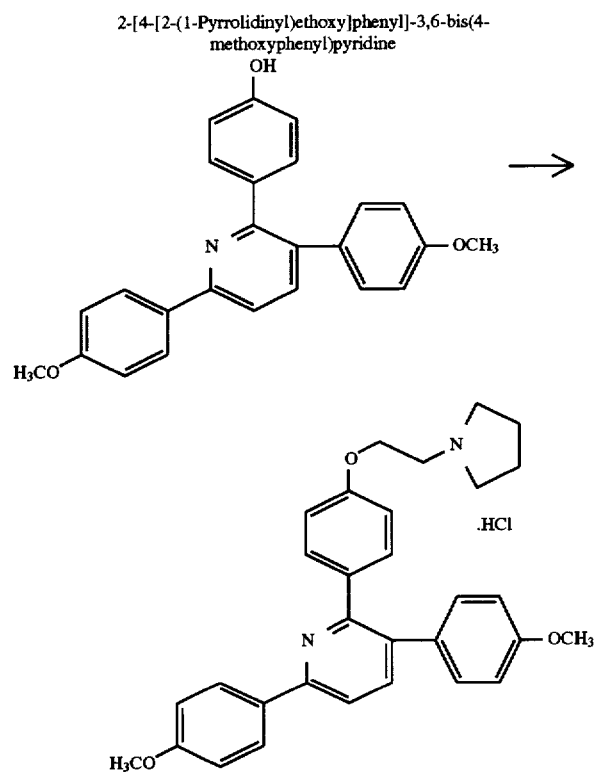

EXAMPLE 6

2-[4-[2-(1-Piperidinyl)ethoxy]phenyl]-3-(4-methoxyphenyl)-6-(4-fluorophenyl)pyridine

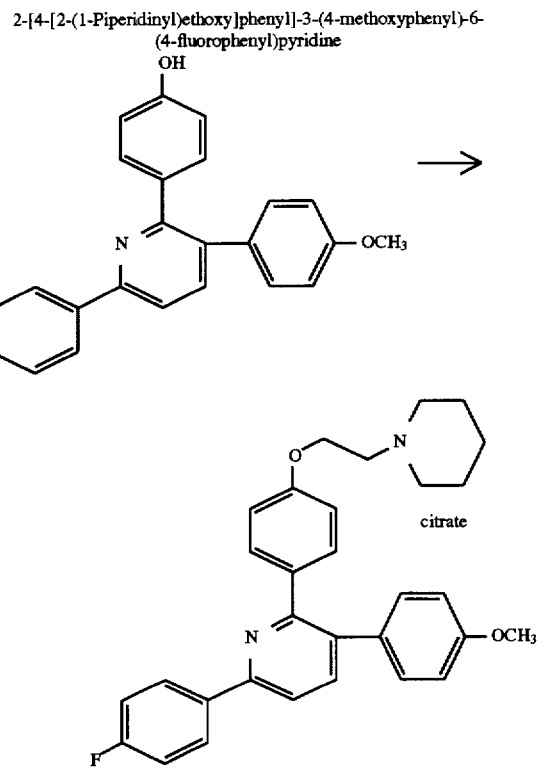

The 2-(4-hydroxyphenyl)-3,6-bis(4-methoxyphenyl) pyridine (2.3 g, 6 mmol), N-(2-chloroethyl)pyrrolidine hydrochloride (1.1 g, 6 mmol), and powdered $K_2CO_3$ (4.1 g, 30 mmol) were stirred in 250 mL methyl ethyl ketone and refluxed 18 h. The TLC (EtOH/$CH_2Cl_2$, 1:4) of the reaction mixture indicated some starting material remained, so more N-(2-chloroethyl)pyrrolidine hydrochloride (0.3 g, 1.6 mmol) and $K_2CO_3$ (2 g, 15 mmol) were added and reaction mixture refluxed an additional 18 h. The reaction mixture was worked up, concentrated, and the residue was dissolved in 25 mL MeOH, treated with 5 mL HCl/MeOH at 0° C., and concentrated. The residue was recrystallised from MeOH/$Et_2O$ to give 1.8 g (58 % yield) of product as the HCl salt: mp 230°–231° C.; $^1$H NMR ($CDCl_3$) d 1.61 (bs, 2H, pyrrolidine), 2.10–2.26 (comp, 4H, pyrrolidine), 2.90–3.10 (bs, 2H, pyrrolidine), 3.48 (bs, 2H, $NCH_2$), 3.84 (s, 3H, $ArOCH_3$), 3.88 (s, 3H, $ArOCH_3$), 4.10–4.14 (m, 2H, $OCH_2$), 6.78–6.81 (d, 2H, J=9 Hz, ArH), 6.86–6.89 (d, 2H, J=9 Hz, ArH), 7.00–7.03 (d, 2H, J=9 Hz, ArH), 7.14–7.16 (d, 2H, J=9 Hz, ArH), 7.44–7.46 (d, 2H, J=9 Hz, ArH), 7.66–7.73 (m, 2H, ArH), 8.07–8.10 (d, 2H, J=9 Hz, ArH); MS(FD) 480($M^+$). Anal. Calcd for $C_{31}H_{32}N_2O_3$ HCl: C, 72.01; H, 6.43; N, 5.42. Found: C, 72.02; H, 6.65; N, 5.24.

The 2-(4-hydroxyphenyl)-3-(4-methoxyphenyl)-6-(4-fluorophenyl)pyridine (1.78 g, 4.8 mmol), N-(2-chloroethyl) piperidine hydrochloride (0.88 g, 4.8 mmol), and powdered $K_2CO_3$ (3.3 g, 24 mmol) were stirred in 150 mL methyl ethyl ketone and refluxed 18 h. The reaction mixture was worked up and concentrated to a light yellow gum. The gum was warmed in 50 mL of acetone, citric acid.$H_2O$ (1 equivalent) was added, the clear solution warmed 5 min, then concentrated, triturated with $Et_2O$, filtered, and dried in vacuo to give 1.1 g (48% overall yield) of product as the citrate salt: mp 100° C.; $^1$H NMR ($CDCl_3$) d 1.25–152 (comp, 6H, piperidine), 2.38–2.54 (m, 4H, citrate), 2.73–2.74 (m, 4H, piperidine), 2.2.93–2.95 (bs, 2H, $CH_2N$), 3.49 (s, 3H, $ArOCH_3$), 3.97–4.00 (bs, 2H, $OCH_2$), 6.47–6.53 (m, 4H, ArH), 6.80–6.87 (m,4H, ArH), 7.07–7.10 (m, 2H, ArH), 7.40–7.41 (m, 2H, ArH), 7.78–7.82 (m, 2H, ArH); MS(FAB) 483 $[M+1]^+$ Anal. Calcd for $C_{31}H_{31}N_2O_2F.C_6H_8O_7$: C, 65.87; H, 5.83; N, 4.15. Found: C, 65.90; H, 6.12; N, 4.09.

EXAMPLE 7

2-[4-[2-(1-Piperidinyl)ethoxy]phenyl]-3-(4-methoxyphenyl)-6-methylpyridine

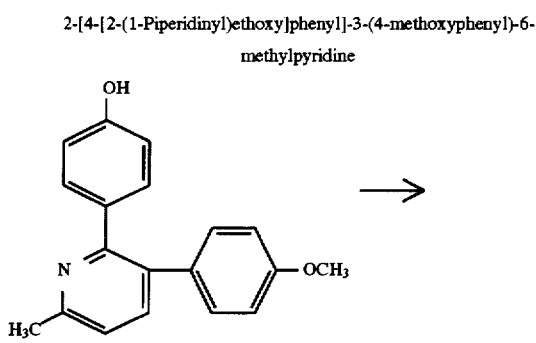

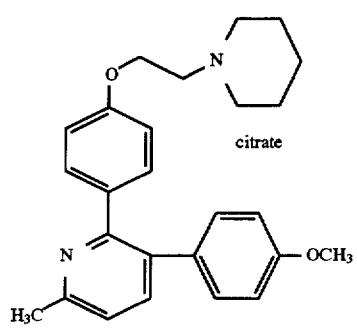

Sodium hydride (60% in mineral oil, 0.26 g, 6.6 mmol) was washed with 2×5 mL hexane, then added portionwise to a solution of the 2-(4-hydroxyphenyl)-3-(4-methoxyphenyl)-6-methylpyridine (1.75 g, 6 mmol) in 60 mL of DMF and stirred at 60° C. for 1 h. A 30 mL DMF solution of N-(2-chloroethyl)piperidine (1.06 g, 7.2 mmol) was added dropwise to the reaction mixture and stirred at 55°–60° C. for 8 h, followed by cooling and quenching with 250 mL of ice water. The aqueous mixture was extracted with EtOAc (3×100 mL) and 100 mL Et$_2$O and the organics were combined, washed with brine, dried (Na$_2$SO$_4$), then concentrated to an oil. The oil was taken up 100 mL Et$_2$O, treated with decolorizing carbon, filtered, and concentrated to give 2.1 g (87% yield) of product as a gum. A portion of the gum (1.3 g, 3.3 mmol) was dissolved in acetone (100 mL), citric acid monohydrate (0.7 g, 3.3 mmol) added, and mixture warmed at gentle reflux for 10 min, then concentrated. The residue was triturated with Et$_2$O, filtered, and dried in vacuo to give 1.7 g (90% conversion of free base to salt) as the solid citrate salt: mp 101°–110° C.; $^1$H NMR (CDCl$_3$+DMSO-d$_6$) d 1.56–1.85 (comp, 6H, piperidine), 2.56 (s, 3H, pyr-CH3), 2.68–2.84 (m, 4H, citrate), 3.06–3.12 (m, 4H, piperidine), 3.28–3.30 (m, 2H, CH$_2$N), 3.74 (s, 3H, ArOCH$_3$), 4.27–4.30 (m, 2H, OCH$_2$), 6.69–6.77 (m, 4H, ArH), 6.99–7.25 (comp, 5H, ArH), 7.50–7.53 (d, 1H, J=8 Hz, ArH); MS(FAB) 403 [M+1]$^+$. Anal. Calcd for C$_{26}$H$_{30}$N$_2$O$_2$·C$_6$H$_8$O$_7$: C, 64.63; H, 6.44; N, 4.71. Found: C, 64.39; H, 6.44; N, 4.93.

EXAMPLE 8

2-[4-[2-(N,N-Dimethylamino)ethoxy]phenyl]-3-(4-hydroxyphenyl)-6-methylpyridine

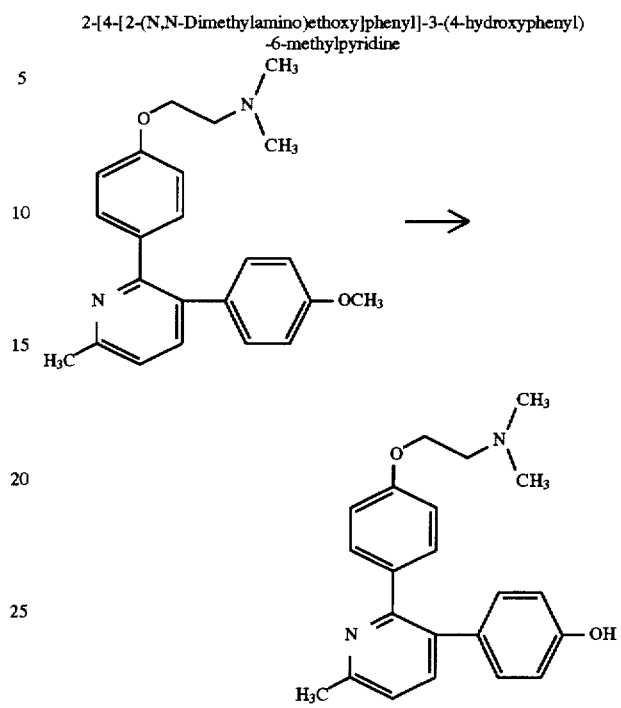

The AlCl$_3$ (7 g, 52 mmol) was stirred in 150 mL of DCE at 0° C., ethanethiol (5.5 mL, 75 mmol) was added, and the mixture stirred for 15 min. The 2-[4-[2-(N,N-dimethylamino)ethoxy]phenyl]-3-(4-methoxyphenyl)-6-methylpyridine (2.7 g, 7.5 mmol) in 50 mL DCE was added dropwise to the reaction mixture and stirred for 2 h as it was allowed to come to rt, then quenched with 25 mL THF at 0° C., followed by 25 mL 1N HCl and worked up. The crude product was recrystallised from hot EtOAc/pet. ether to give 0.9 g (34% yield) of white solid: mp 155°–157° C.; $^1$H NMR (CDCl$_3$) d 2.37 (s, 6H, NCH$_3$), 2.62 (s, 3H, pyr-CH$_3$), 2.78–2.81 (t, 2H, J=5 Hz, CH$_2$N), 4.05–4.07 (t, 2H, J=5 Hz, OCH$_2$), 6.64–6.69 (m, 4H, ArH), 6.94–6.96 (d, 2H, J=8 Hz, ArH), 7.09–7.12 (d, 1H, J=8 Hz, ArH), 7.24–7.27 (comp, 2H, ArH), 7.52–7.55 (d, 1H, J=8 Hz, ArH); MS(FD) 348 (M$^+$) Anal. Calcd for C$_{22}$H$_{24}$N$_2$O$_2$: C, 75.84; H, 6.94; N, 8.04. Found: C, 75.70; H, 6.98; N, 8.00.

EXAMPLE 9

2-[4-[2-(1-Pyrrolidinyl)ethoxy]phenyl]-3-(4-hydroxyphenyl)-6-methylpyridine

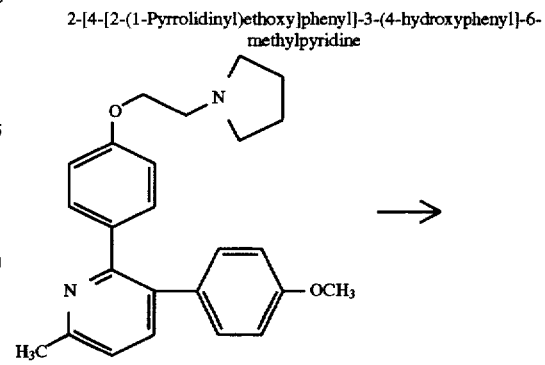

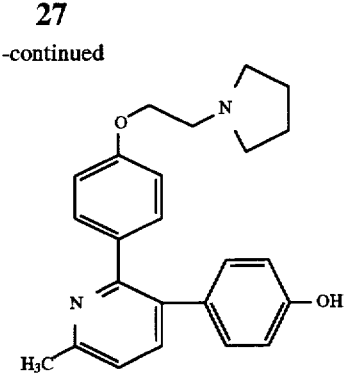

The AlCl₃ (3.6 g, 27 mmol) was stirred in 100 mL of DCE at 0° C., ethanethiol (3 mL, 38 mmol) was added, and the mixture stirred for 15 min. The 2-[4-[2-(1-pyrrolidinyl)ethoxy]phenyl]-3-(4-methoxyphenyl)-6-methylpyridine (1.5 g, 3.9 mmol) in 50 mL DCE was added dropwise to the reaction mixture and stirred for 2 h as it was allowed to come to rt, then quenched with 75 mL THF at 0° C., followed by 50 mL 1N HCl and worked up. The crude product was triturated with Et₂O, filtered, and dried in vacuo to give 1.3 g (90% yield) of an off-white solid: mp 159°–161° C.; $^1$H NMR (CDCl₃) d 1.80–184 (bs, 4H, pyrrolidine), 2.61 (s, 3H, pyr-CH₃), 2.67–2.69 (bs, 4H, pyrrolidine), 2.93–2.97(m, 2H, CH₂N), 4.08–4.10 (m, 2H, OCH₂), 6.60–6.65 (m, 4H, ArH), 6.90–6.93 (d, 2H, J=8 Hz, ArH), 7.08–7.11 (d, 1H, J=8 Hz, ArH), 7.23–7.26 (m, 2H, ArH), 7.50–7.53 (d, 1H, J=8 Hz, ArH); MS(FD) 374(M⁺). Anal. Calcd for C₂₄H₂₆N₂O₂: C, 76.98; H, 7.00; N, 7.48. Found: C, 76.70; H, 7.07; N, 7.36.

EXAMPLE 10

2-[4-[2-(1-Piperidinyl)ethoxy]phenyl]-3-(4-hydroxyphenyl)-6-methylpyridine

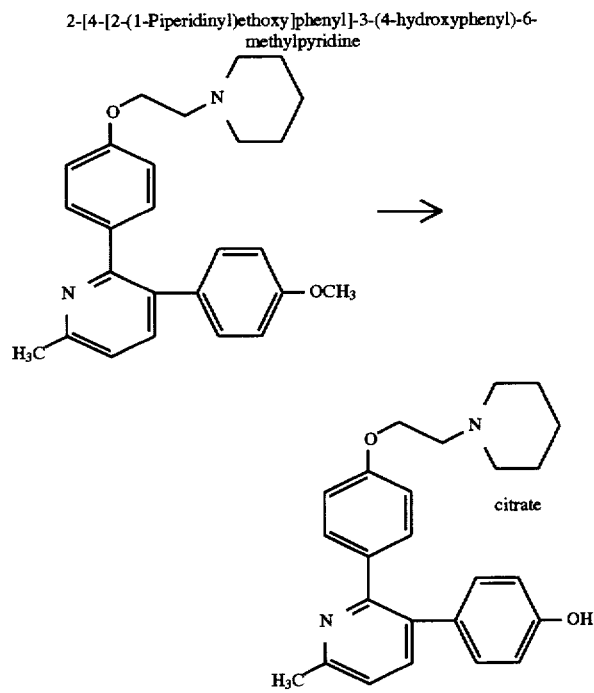

The AlCl₃ (1.2 g, 9 mmol) was stirred in 30 mL of DCE at 0° C., ethanethiol (1 mL, 14 mmol) was added, and the mixture stirred for 15 min. The 2-[4-[2-(1-piperidinyl)ethoxy]phenyl]-3-(4-methoxyphenyl)-6-methylpyridine (0.5 g, 1.2 mmol) in 20 mL DCE was added dropwise to the reaction mixture and stirred for 2 h as it was allowed to come to rt, then quenched with 25 mL THF at 0° C., followed by 25 mL 1N HCl and worked up. The free base gave a very clean NMR, but the elemental analysis was low for carbon and hydrogen, so it was taken up in 50 mL hot acetone, citric acid.H₂O (0.2 g, 0.9 mmol) was added, then heated 10 min, concentrated, triturated with Et₂O, filtered, and dried in vacuo to give 0.38 g (72% yield) of product as the citrate salt: mp 90°–100° C.; $^1$H NMR (CDCl₃) (free base) d 1.34–1.66 (comp, 6H, piperidine), 2.42–2.65 (comp, 7H, pyr-CH₃ and piperidine), 2.70–2.79 (m, 2H, CH₂N), 3.95–4.10 (m, 2H, OCH₂), 6.50–6.59 (m, 4H, ArH), 6.76–6.85 (d, 2H, J=8 Hz, ArH), 6.98–7.05 (d, 1H, J=8 Hz, ArH), 7.10–7.21 (m, 2H, ArH), 7.41–7.50 (d, 1H, J=8 Hz, ArH); MS(FAB) 398 [M+1]⁺. Anal. Calcd for C₂₅H₂₈N₂O₂.C₆H₈O₇: C, 64.13; H, 6.25; N, 4.82. Found: C, 63.99; H, 6.36; N, 4.58.

EXAMPLE 11

2-[4-[2-(4-Morpholinyl)ethoxy]phenyl]-3-(4-hydroxyphenyl)-6-methylpyridine

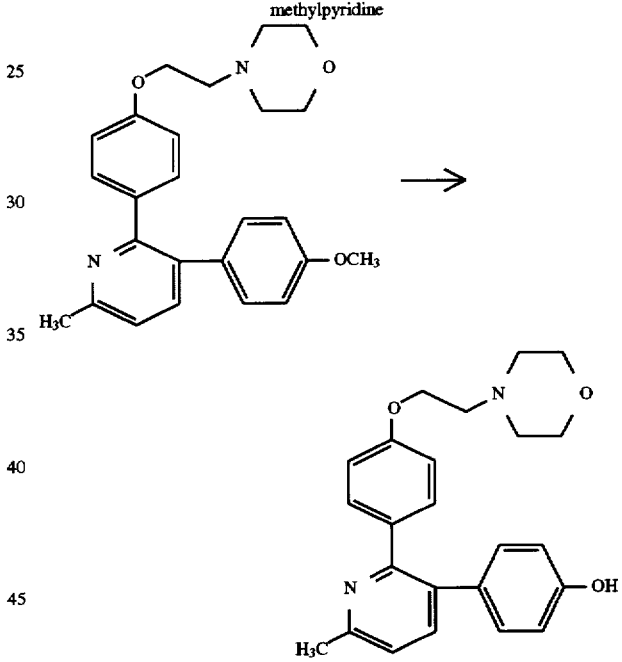

The AlCl₃ (5 g, 38 mmol) was stirred in 100 mL of DCE at 0° C., ethanethiol (4 mL, 54 mmol) was added, and the mixture stirred for 15 min. The 2-[4-[2-(4-morpholinyl)ethoxy]phenyl]-3-(4-methoxyphenyl)-6-methylpyridine (2.2 g, 5.4 mmol) in 50 mL DCE was added dropwise to the reaction mixture and stirred for 2 h as it was allowed to come to rt, then quenched with 50 mL THF at 0° C., followed by 50 mL 1N HCl and worked up. The crude product was triturated with Et₂O/pet. ether, filtered, and dried in vacuo to give 1.9 g (90 % yield) of white solid: mp 75°–80° C.; $^1$H NMR (CDCl₃) d 2.59–2.62 (comp, 7H, morpholine and pyr-CH₃), 2.79–2.83 (t, 2H, J=5 Hz, CH₂N), 3.74–3.77 (m, 4H, morpholine), 4.07–4.11 (t, 2H, J=5 Hz, OCH₂), 6.63–6.71 (m, 4H, ArH), 6.94–6.97 (d, 2H, J=8 Hz, ArH), 7.11–7.13 (d, 1H, J=8 Hz, ArH), 7.24–7.27 (d, 2H, J=8 Hz, ArH), 7.53–7.56 (d, 1H, J=8 Hz, ArH); MS(FD) 390 (M⁺). Anal. Calcd for C₂₄H₂₆N₃O₃: C, 73.82; H, 6.71; N, 7.17. Found: C, 73.75; H, 6.71; N, 7.05.

EXAMPLE 12

2-[4-[2-(1-Piperidinyl)ethoxy]phenyl]-3-(4-hydroxyphenyl)-6-(4-fluorophenyl)pyridine

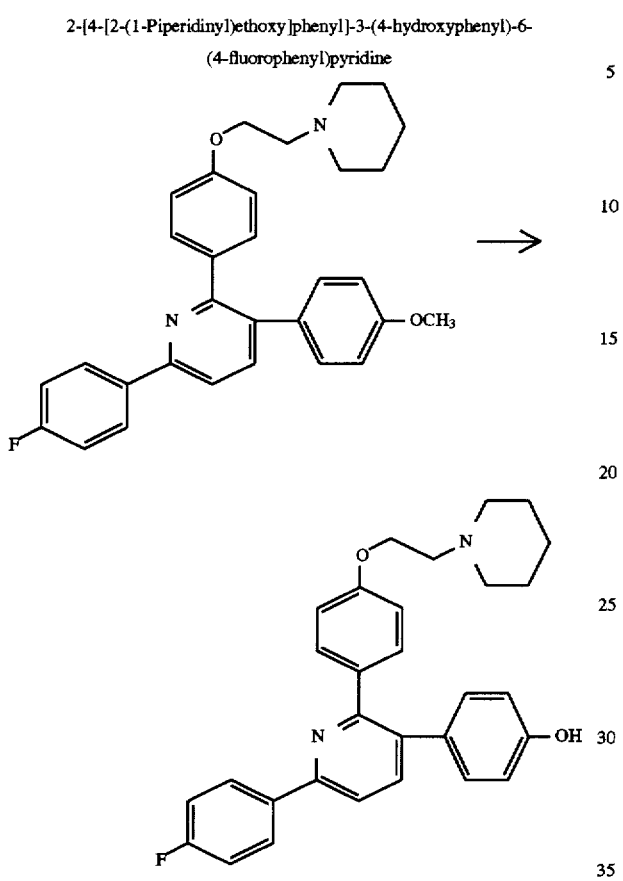

The AlCl₃ (1.9 g, 14 mmol) was stirred in 50 mL of DCE at 0° C., ethanethiol (1.5 mL, 20 mmol) was added, and the mixture stirred for 15 min. The 2-[4-[2-(1-piperidinyl)ethoxy]phenyl]-3-(4-methoxyphenyl)-6-(4-fluorophenyl)pyridine (1 g, 2 mmol) in 25 mL DCE was added dropwise to the reaction mixture and stirred for 2 h as it was allowed to come to rt, then quenched with 25 mL THF at 0° C., followed by 25 mL 1N HCl and worked up. The crude product was triturated with Et₂O, filtered, and dried in vacuo to give 0.86 g (91% yield) of white solid: mp 194°–195° C.; $^1$H NMR (CDCl₃) d 1.63–167 (comp, 6H, piperidine), 2.59 (bs, 4H, piperidine), 2.81–2.84 (t, 2H, J=5 Hz, CH₂N), 4.12–4.15 (t, 2H, J=5 Hz, OCH₂), 6.64–6.70 (m, 4H, ArH), 7.00–7.03 (d, 2H, J=8 Hz, ArH), 7.12–7.18 (m, 2H, ArH), 7.37–7.40 (d, 2H, J=8 Hz, ArH), 7.61–7.67 (m, 2H, ArH), 8.08–8.12 (m, 2H, ArH); MS (FD) 468 (M⁺). Anal. Calcd for C₃₀H₂₉N₂O₂ F: C, 76.90; H, 6.24; N, 5.98. Found: C, 77.13; H, 6.36; N, 5.86.

EXAMPLE 13

2-[4-[2-(1-Pyrrolidinyl)ethoxy]phenyl]-3-(4-hydroxyphenyl)-6-phenylpyridine

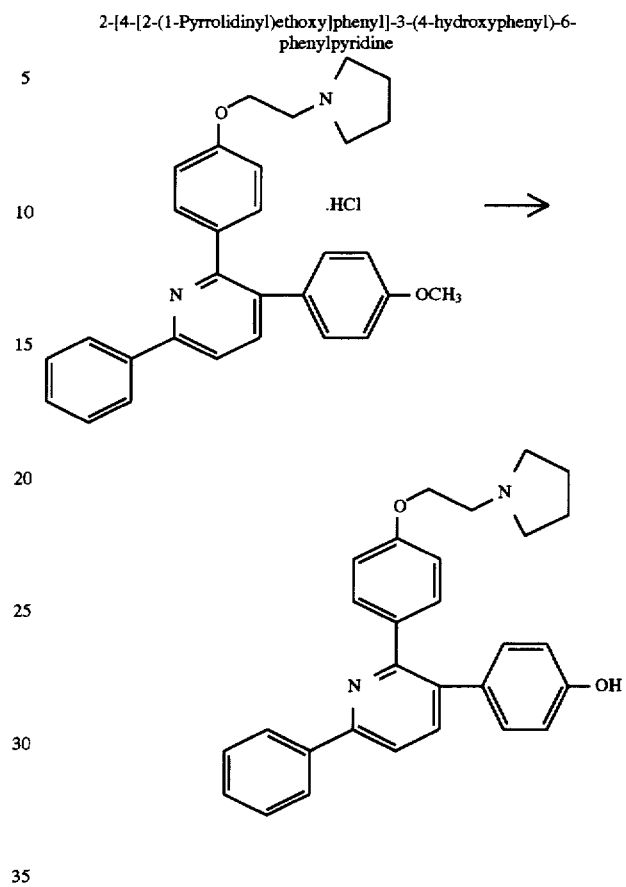

The 2-[4-[2-(1-pyrrolidinyl)ethoxy]phenyl]-3-(4-methoxyphenyl)-6-phenylpyridine as the HCl salt (1.9 g, 3.9 mmol) was slurried with 50 mL of DCE in a screw cap flask, cooled to 0° C., and stirred while the BCl₃ (2.7 mL at 0° C., 32 mmol) in 5 mL DCE was added and the reaction flask sealed. After 2 h, TLC (EtOH/CH₂Cl₂, 1:4) indicated that starting material remained, so an additional 1.7 mL of BCl₃ (20 mmol) was added and reaction mixture stirred for 18 h. The reaction mixture was carefully quenched with 25 mL MeOH at 0° C., poured in 150 mL of aqueous NaHCO₃, and extracted with CH₂Cl₂ (3×100 mL). The CH₂Cl₂ extracts were combined, washed with brine, dried (Na₂SO₄), concentrated, and recrystallised from EtOH to give 1.35 g (79% yield) of product: mp 176°–178° C.; $^1$H NMR (CDCl₃) d 1.86 (bs, 4H, pyrrolidine), 2.73(bs, 4H, pyrrolidine), 2.97–3.01 (t, 2H, J=5 Hz, CH₂N), 4.12–4.16 (t, 2H, J=5 Hz, OCH₂), 6.64–6.67 (m, 4H, ArH), 6.98–7.01 (d, 2H, J=8 Hz, ArH), 7.38–7.50 (m, 5H, ArH), 7.67 (s, 2H, ArH), 8.10–8.12 (d, 2H, J=8 Hz, ArH); MS(FD) 436 (M⁺). Anal. Calcd for C₂₉H₂₈N₂O₂: C, 79.79; H, 6.46; N, 6.42. Found: C, 80.01; H, 6.55; N, 6.54.

EXAMPLE 14

2-[4-[2-(1-Pyrrolidinyl)ethoxy]phenyl]-3,6-bis(4-hydroxyphenyl)pyridine

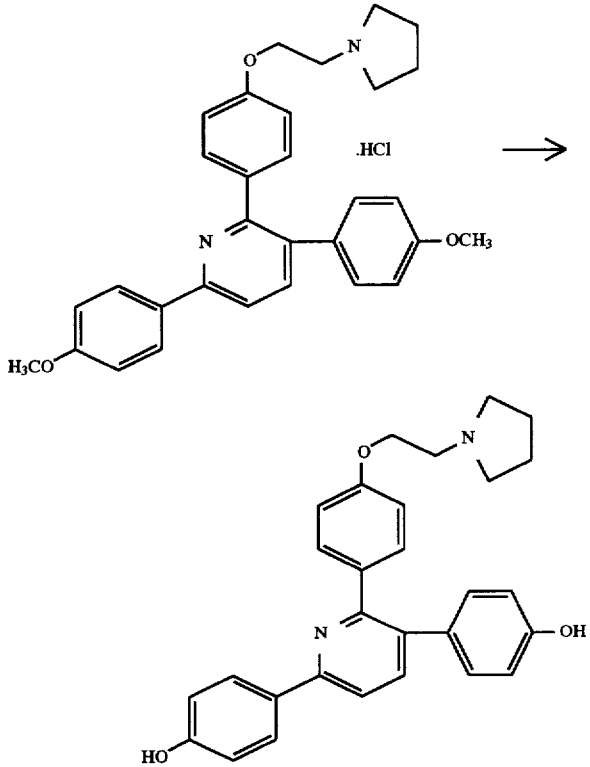

The 2-[4-[2-(1-pyrrolidinyl)ethoxy]phenyl]-3,6-bis(4-methoxyphenyl)pyridine as the HCl salt (1.1 g, 2.1 mmol) was slurried with 50 mL of DCE in a screw cap flask, cooled to 0° C., and stirred while the $BCl_3$ (5.5 mL at 0° C., 64 mmol) was added, the reaction flask sealed, and reaction mixture stirred for 20 h. The reaction mixture was carefully quenched with 25 mL MeOH at 0° C., poured in 150 mL of aqueous $NaHCO_3$, and extracted with $CH_2Cl_2$ (3×100 mL). The $CH_2Cl_2$ extracts were combined, washed with brine, dried ($Na_2SO_4$), concentrated, and recrystallised from EtOH to give 0.89g (83% yield) of product: mp 145°–150° C.; $^1H$ NMR ($CDCl_3$) d 1.63 (bs, 2H, pyrrolidine), 2.01–2.76 (comp, 6H, pyrrolidine and $CH_2N$), 3.90–3.94 (m, 2H, $OCH_2$), 6.55–6.60 (m, 4H, ArH), 6.6.71–6.84 (m, 4H, ArH), 7.19–7.22 (d, 2H, J=9 Hz, ArH) 7.43–7.45 (m, 2H, ArH), 7.76–7.79 (d, 2H, J=9 Hz, ArH); MS(FD) 452 ($M^+$). Anal. Calcd for $C_{29}H_{28}N_2O_3$: C, 76.97; H, 6.24; N, 6.19. Found: C, 76.92; H, 6.18; N, 6.13.

Test Procedure

General Preparation Procedure

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.70° C. with a minimum relative humidity of 40%. The photoperiod in the room was 12 hours light and 12 hours dark.

Dosing Regimen Tissue Collection

After a one week acclimation period (therefore, two weeks post-OVX) daily dosing with test compound was initiated. 17α-ethynyl estradiol or the test compound were given orally, unless otherwise stated, as a suspension in 1%. carboxymethylcellulose or dissolved in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Uterine Eosinophil Peroxidase (EPO) Assay

Uteri were kept at 4° C. until time of enzymatic analysis. The uteri were then homogenized in 50 volumes of 50 mM Tris buffer (pH −8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosinophils in the uterus is an indication of estrogenic activity of a compound. The maximal velocity of a 15 second interval was determined over the initial, linear portion of the reaction curve.

Source of Compound

17α-ethynyl estradiol was obtained from Sigma Chemical Co., St. Louis, Mo.

Influence of Formula I Compounds on Serum Cholesterol and Determination of Aponist/Non-Agonist Activity Data presented in Table 1 below show comparative results among ovariectomized rats, rats treated with 17α-ethynyl estradiol ($EE_2$; an orally available form of estrogen), and rats treated with certain compounds of the present invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized control animals. This uterine response to estrogen is well recognized in the art.

Not only did the compounds of the present invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the below data, estrogenicity also was assessed by evaluating the response of eosinophil infiltration into the uterus. Most of the compounds of the present invention did not cause any increase in the number of eosinophils observed in the stromal layer of ovariectomized rats, while others caused only modest increases. Estradiol caused a substantial, expected increase in eosinophil infiltration.

The data presented in Table 1 below reflects the response of 5 to 6 rats per treatment. "NA" indicates that a compound was not active at the doses tested.

TABLE 1

| Compound | Dose (mg/kg) | Uterine Wt. (% inc. vs. OVX) | Uterine EPO (V. max) | Serum Cholesterol (% dec. vs. OVX) | ED50 (effective dose to dec. serum chol. by 50%) |
|---|---|---|---|---|---|
| EE2 | 0.1 | 221.8* | 235.6* | 88.3* | |
| Example 6 | 1 | 15.6 | 3.7 | 12.3 | |
|  | 10 | 44.2 | 5.8 | −9.1 | |
|  | 25 | 69.5* | 22.6* | 40.8* | 70 |
| EE2 | 0.1 | 183.3* | 339.2* | 86.9* | |
| Example 6 | 0.1 | 9.5 | 6.6 | 4 | |
|  | 1 | −2.4 | 5.9 | 7.4 | |
|  | 10 | 47.6* | 6.5 | 33.1* | 105 |
| EE2 | 0.1 | 122.3* | 79.0* | 83.1* | |
| Example 12 | 0.1 | 9.8 | 5.9 | 26.2 | |
|  | 1 | 4.2 | 9.7 | 9.8 | |
|  | 10 | 76.2* | 43.9* | 0.1 | NA |
| EE2 | 0.1 | 125.8* | 44.9* | 83.3* | |
| Example 12 | 1 | 2.5 | 5.4 | 24.7* | |
|  | 10 | 62.5* | 70.1* | 60.6* | |
|  | 25 | 68.0* | 67.9* | 49.9* | 1.5 |
| EE2 | 0.1 | 118.2* | 153.9* | 96.4* | |
| Example 5 | 0.1 | −6.5 | 4.5 | 2.4 | |
|  | 1 | −7.6 | 4.2 | 14 | |
|  | 10 | 27.2* | 23.1 | 23.5* | >10 |
| EE2 | 0.1 | 118.2* | 153.9* | 96.4* | |
| Example 14 | 0.1 | 6.3 | 2.4 | 11.9 | |
|  | 1 | −3.3 | 4.5 | −16.5 | |
|  | 10 | 8.8 | 4.2 | −7.3 | NA |
| EE2 | 0.1 | 105.6* | 140.4* | 71.4* | |
| Example 13 | 1 | 54.0* | 61.8* | 53.8* | |
|  | 10 | 38.8* | 39.0 | 36.8* | |
|  | 25 | 35.5* | 53.4* | 62.6* | <1 |
| EE2 | 0.1 | 93.8* | 207.6* | 68.0* | |
| Example 13 | 0.1 | 23.8 | 4.5 | 1.8 | |
|  | 1 | 61.9* | 34.8 | 50.9* | |
|  | 10 | 47.4* | 32.1 | 55.6* | |
|  | 25 | 46.6* | 22.2 | 39.4* | ED50 ~ 1 |
| EE2 | 0.1 | 125.8* | 111.2* | 88.1 | |
| Example 3 | 1 | 4.9 | 10.8* | 4.5 | |
|  | 10 | −6.1 | 6 | 1.4 | |
|  | 25 | −2.3 | 3.8 | −11.6 | NA |
| EE2 | 0.1 | 144.0* | 185.7* | 90.1* | |
| Example 11 | 1 | −0.8 | 4.8 | 16 | |
|  | 10 | 27 | 4.9 | 18.2 | |
|  | 25 | 5 | 4.4 | −3.6 | NA |
| EE2 | 0.1 | 104.5* | 20.4* | 90.5* | |
| Example 10 | 1 | 3.4 | 4.4 | 8.4 | |
|  | 10 | 7 | 3.4 | 1.7 | |
|  | 25 | 47.0* | 6.8* | 17.9 | NA |
| EE2 | 0.1 | 82.2* | 192.9 | 85.4* | |
| Example 7 | 0.1 | −2.2 | 4.1 | 23.2 | |
|  | 1 | 64.4* | 19.1* | 51.8* | |
|  | 10 | −2.2 | 2.5 | 25.9 | 1 |
| EE2 | 0.1 | 132.1* | 349.8* | 90.5* | |
| Example 7 | 0.1 | 0.4 | 7.3 | 27.7* | |
|  | 1 | −0.4 | 17.3* | 17.5 | |
|  | 10 | 10.7 | 9.1 | 34.0* | 11 |
| EE2 | 0.1 | 144.0* | 185.7* | 90.1* | |
| Example 7 | 1 | 16.4 | 3.1 | −35.5* | |
|  | 10 | 5.4 | 3.6 | −5.2 | |
|  | 25 | −5.6 | 3.6 | −1.2 | NA |
| EE2 | 0.1 | 102.2* | 62.7* | 82.9* | |

TABLE 1-continued

| Compound | Dose (mg/kg) | Uterine Wt. (% inc. vs. OVX) | Uterine EPO (V. max) | Serum Cholesterol (% dec. vs. OVX) | ED50 (effective dose to dec. serum chol. by 50%) |
|---|---|---|---|---|---|
| Example 2 | 1 | 12.7 | 6.6 | −23.6 | |
|  | 10 | −12.5 | 5.9 | −33.5 | |
|  | 25 | 19.5* | 59.8 | 9.7 | NA |
| EE2 | 0.1 | 125.8* | 44.9* | 83.3* | |
| Example 9 | 1 | 2 | 6.7 | 23* | |
|  | 10 | 26.3* | 10.2 | 49.2* | |
|  | 25 | 24.3* | 8.5 | 58.5* | 2.2 |
| EE2 | 0.1 | 144.0* | 185.7* | 90.1* | |
| Example 9 | 1 | 6.2 | 4.6 | −2 | |
|  | 10 | 30.3* | 4.4 | 29.5* | |
|  | 25 | 35.1* | 5.6 | 50.0* | 28 |
| EE2 | 0.1 | 223.2* | 265.2* | 91.2* | |
| Example 1 | 1 | 0.6 | 2.9 | 15 | |
|  | 10 | 2.6 | 2.5 | 14.9 | |
|  | 25 | 5.2 | 2.3 | 22.2* | >1000 |
| EE2 | 0.1 | 144.0* | 185.7* | 90.1* | |
| Example 8 | 1 | −1.5 | 5 | 15.7 | |
|  | 10 | −1 | 6.7 | 1.5 | |
|  | 25 | 41.6* | 58.6* | 46.4* | 26 |

*P = ≦ 0.5 ANOVA with post-hoc Fisher's PLSD on raw data

In addition to the demonstrated benefits of the compounds of the present invention, especially when compared to estradiol, the above data clearly demonstrate that compounds of Formula I are not estrogen mimetics. Furthermore, no deleterious toxicological effects (survival) were observed with any treatment.

Osteoporosis Test Procedure

Following the General Preparation Procedure, infra, the rats were treated daily for 35 days (6 rats per treatment group) and sacrificed by carbon dioxide asphyxiation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen dificiency associated with complete ovariectomy. Uterine weight was routinely reduced about 75% in response to ovariectomy.

The right femurs were excised and digitilized x-rays generated and analyzed by an image analysis program (NIH image) at the distal metaphysis. The proximal aspect of the tibiae from these animals were also scanned by quantitative computed tomography.

In accordance with the above procedures, the compound of Example 9 and ethynyl estradiol (EE$_2$) in 20% hydroxypropyl β-cyclodextrin were orally administered to test animals. Distal femur metaphysis data presented in Tables 2 and 3 below are the results of compound treatments compared to intact and ovariectomized test animals. The rats in the Table 2 tests were 6 months of age rather than 75 days of age (at the beginning of the tests).

TABLE 2

| Compound | Dose (mg/kg) | Body Wt.Change (% dec. vs. OVX) | Uterine Wt. (% inc. vs. OVX) | Femur (x-ray image) (% protect.) | Serum Chol. (% dec. vs. OVX) |
|---|---|---|---|---|---|
| EE2 | 0.1 | 22.4* | 128.3* | 41.8* | 73.8* |
| Example 9 | 1 | 8.3 | −8.6 | 5.9 | 35.4* |
|  | 10 | 4.5 | 4.3 | −15.3 | 35.4* |

TABLE 2-continued

| Compound | Dose (mg/kg) | Body Wt.Change (% dec. vs. OVX) | Uterine Wt. (% inc. vs. OVX) | Femur (x-ray image) (% protect.) | Serum Chol. (% dec. vs. OVX) |
|---|---|---|---|---|---|
|  | 25 | 6.3 | −6.8 | 33.3 | 19.7 |
| EE2 | 0.1 | 59.1* | 226.1* | 25.5* | 73.6* |
| Example 9 | 0.01 | −5 | −3.5 | −11.5 | 44.4* |
|  | 0.1 | −8.2 | −11 | −16.4* | 33.6* |
|  | 1 | 13.4 | 17.4 | −9.9 | 54.2* |
|  | 10 | 29.6 | 62.0 | 28.1 | 42.2* |

*P = ≦ 0.5 ANOVA with post-hoc Fisher's PLSD on raw data

In summary, ovariectomy of the test animals caused a significant reduction in femur density compared to intact, vehicle treated controls. Orally administered ethynyl estradiol ($EE_2$) prevented this loss, but the risk of uterine stimulation with this treatment is ever-present.

The compound of Example 9 of the present invention elevated mean bone density in a general, dose-related manner. Accordingly, the compounds of the present invention are useful for the treatment of post-menopausal syndrome, particularly osteoporosis.

MCF-7 Proliferation Assay

MCF-7 breast adenocarcinoma cells (ATCC HTB 22) were maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium ($Ca++/Mg++$ free HBSS (phenol red-free) supplemented with 10 mM HEPES and 2 mM EDTA). Cells were washed twice with assay medium and adjusted to 80,000 cells/mL. Approximately 100 µL (8,000 cells) were added to flat-bottom microculture wells (Costar 3596) and incubated at 37° C. in a 5% $CO_2$ humified incubator for 48 hours to allow for cell adherence and equilbration after transfer. Serial dilutions of drugs or DMSO as a diluent control were prepared in assay medium and 50 µL transferred to triplicate microcultures followed by 50 µL assay medium for a final volume of 200 µL. After an addition 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wailac BetaPlace β counter. Results in Table 4 below show the $IC_{50}$ for certain compounds of the present invention.

TABLE 4

| Compound (Example Reference) | $IC_{50}$ nM |
|---|---|
| 1 | 1000 |
| 2 | 1000 |
| 3 | 1000 |
| 5 | 1000 |
| 6 | 470 |

TABLE 4-continued

| Compound (Example Reference) | $IC_{50}$ nM |
|---|---|
| 7 | 1000 |
| 8 | 1000 |
| 9 | 1000 |
| 11 | 1000 |
| 12 | 185 |
| 14 | 9 |

Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of fibroid tumors in guinea pig

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri are harvested to assess the status of the organ.

Test 5

A. Tissue from human uterine fibroid tumors is harvested and maintained, in vitro, as primary nontransformed cultures Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component $C_3$ and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical induction of endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric gavage on a daily basis for 3–16 weeks, and implants are removed and measured for growth or regression. At the time of sacrifice, the intact horn of the uterus is harvested to assess status of endometrium.

B. Implantation of human endometrial tissue in nude mice

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric gavage on a daily basis for 3–16 weeks, and implants are removed and measured for growth or regression. At the time of sacrifice, the uteri are harvested to assess the status of the intact endometrium.

Test 4

A. Tissue from human endometrial lesions is harvested and maintained in vitro as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Inhibition of Aortal Smooth Cell Proliferation/Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $C_{O2}$/95% air. At the end of 24 hours, the cells are fixed in methanol. $^3$H thymidine incorporation in DNA is then determined by scintillation counting as described in Bonin, et al., *Exp. Cell Res.* 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above tests indicates that the compounds of the present invention are of potential in the treatment of restenosis.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

As used herein, the term "estrogen" includes steroidal compounds having estrogenic activity such as, for example, 17β-estradiol, estrone, conjugated estrogen (Premarin®), equine estrogen, 17α-ethynyl estradiol, and the like. As used herein, the term "progestin" includes compounds having progestational activity such as, for example, progesterone, norethynodrel, norgestrel, megestrol acetate, norethindrone, and the like.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethynodrel (1.0–10.0 mg/day), and norethindrone (0.5–2.0 mg/day). A preferred estrogen-based compound is Premarin, and norethynodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 1000 mg/day of a compound of the present invention. Preferred daily doses generally will be from about 15 mg to about 500 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation. The following formulation examples only are illustrative and are not intended to limit the scope of the present invention.

Formulations

In the formulations which follow, "active ingredient" means a compound of Formula I, or a salt or solvate thereof. Formulation 1: Gelatin Capsules Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |

41
-continued

| Ingredient | Quantity (mg/tablet) |
|---|---|
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:
Formulation 4: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:
Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:
Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

42

An intravenous formulation is prepared as follows:
Formulation 7: Intravenous Solution

| Ingredient | Quantity |
|---|---|
| Active ingredient | 50 mg |
| Isotonic saline | 1,000 mL |

The solution of the above ingredients is intravenously administered to a patient at a rate of about 1 mL per minute.
Formulation 8: Combination Capsule I

| Ingredient | Quantity (mg/capsule) |
|---|---|
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
|---|---|
| Active ingredient | 50 |
| Norethynodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
|---|---|
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:
1. A process for preparing a compound of Formula Ia:

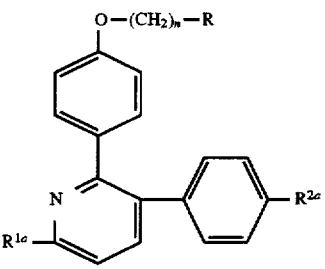

wherein:
n is 2 or 3;
R is dimethylamino, diethylamino, 1-piperidinyl, 1-pyrrolidinyl, 4-morpholinyl, or 1-hexamethyleneimino;
$R^{1a}$ is hydrogen, loweralkyl of $C_1-C_4$, phenyl, or mono- or disubstituted phenyl wherein each substituent is independently halo, methyl, $C_1-C_6$-alkoxy, benzyloxy, $C_1$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, or $C_4$–$C_6$-alkylsulfonyloxy;

$R^{2a}$ is hydrogen, $C_1$–$C_6$-alkoxy, benzyloxy, $C_1$–$C_6$ alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, or $C_4$–$C_6$-alkysulfonyloxy, which comprises reacting a compound of Formula II:

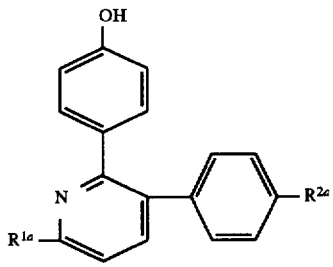

with an alkyl chloride of the formula Cl—$(CH_2)_n$—R, in an inert solvent, in the presence of base, and at a temperature of from 0° to 100° C.

2. The process of claim 1 comprising a subsequent step of deprotecting a protected hydroxy substituent.

3. The process of claim 2 for making 2-[4-(2-(1-pyrrolidinyl)ethoxy]phenyl]-3-(4-hydroxyphenyl)-6-methylpyridine.

4. A compound of Formula II:

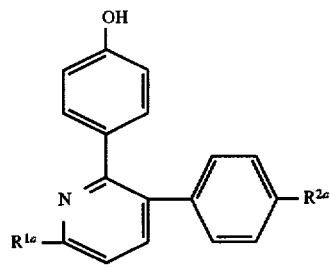

wherein:

$R^{1a}$ is hydrogen, loweralkyl of $C_1$–$C_4$, phenyl, or mono- or disubstituted phenyl wherein each substituent is independently halo, methyl, $C_1$–$C_6$-alkoxy, benzyloxy, $C_1$–$C_6$-alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, or $C_4$–$C_6$-alkylsulfonyloxy; and $R^{2a}$ is hydrogen, $C_1$–$C_6$-alkoxy, benzyloxy, $C_1$–$C_6$ alkanoyloxy, benzoyloxy, substituted benzoyloxy bearing 1 to 3 substituents each of which is independently halo, $C_1$–$C_4$-loweralkyl, or $C_1$–$C_4$-loweralkoxy, $C_1$–$C_5$-alkoxycarbonyloxy, or $C_4$–$C_6$ alkylsulfonyloxy.

* * * * *